United States Patent

Hajos

[11] 4,061,679
[45] * Dec. 6, 1977

[54] STEREOSPECIFIC TOTAL STEROIDAL SYNTHESIS VIA SUBSTITUTED C/D-TRANS INDANONES

[75] Inventor: Zoltan George Hajos, Upper Montclair, N.J.

[73] Assignee: Hoffmann-La Roche Inc., Nutley, N.J.

[*] Notice: The portion of the term of this patent subsequent to Oct. 5, 1993, has been disclaimed.

[21] Appl. No.: 705,306

[22] Filed: July 14, 1976

Related U.S. Application Data

[62] Division of Ser. No. 482,711, June 24, 1974, Pat. No. 3,984,474, which is a division of Ser. No. 765,023, Oct. 4, 1968, Pat. No. 3,897,460.

[51] Int. Cl.² ............................................. C07C 49/54
[52] U.S. Cl. ............................................... 260/586 F
[58] Field of Search ....................... 260/586 F, 586 E

[56] References Cited

U.S. PATENT DOCUMENTS

| | | | |
|---|---|---|---|
| 3,658,847 | 4/1972 | Fried | 260/586 F |
| 3,816,458 | 6/1974 | Saucy | 260/586 F |
| 3,821,308 | 6/1974 | Los | 260/586 F |
| 3,984,473 | 10/1976 | Hojos | 260/586 F |

*Primary Examiner*—Bernard Helfin
*Assistant Examiner*—James H. Reamer
*Attorney, Agent, or Firm*—Samuel L. Welt; George M. Gould; Raymond R. Wittekind

[57] ABSTRACT

Total synthesis of known progestationally active steroidal materials. The steroids can be synthesized depending on the particular starting reactants selected by employing as intermediates bicyclic compounds of the formula

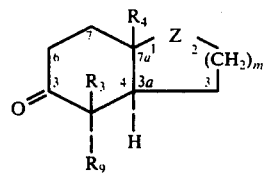

wherein $m$ is an integer having a value of 1 or 2; $R_4$ is hydrogen or lower alkyl; Z is lower alkylenedioxy, $CH(OR_2)$ and carbonyl; $R_8$ when taken alone is hydrogen; $R_9$ when taken alone is lower alkoxycarbonyl, aryloxy-carbonyl, lower cycloalkyloxycarbonyl, carbonyl-halide, hydrogen, carboxy, formyl and methylene-X, where X is a leaving group and when taken together are methylene; with the proviso that when Z is carbonyl $R_8$ when taken alone is hydrogen; $R_9$ when taken alone is carbonyl halide, hydrogen, carboxy, formyl and methylene-X where X is a leaving group and when taken together are methylene and $R_2$ is hydrogen, lower alkyl, lower alkoxy-lower alkyl, phenyl-lower alkyl, tetrahydropyranyl, lower alkanoyl, benzoyl, nitrobenzoyl, carboxy-lower alkanoyl, carboxybenzoyl, trifluoroacetyl and camphorsulfonyl and reacting them in the case where $R_8$ and $R_9$ taken together are methylene or $R_8$ is hydrogen and $R_9$ is methylene-X with β-keto esters and other analogs of the formula

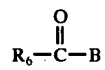

wherein $R_6$ is selected from the group consisting of

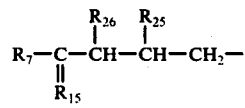

and lower alkyl; $R_7$ is lower alkyl; $R_{15}$ is selected from the group consisting of oxo, lower alkylenedioxy or (hydrogen and lower alkoxy); B is selected from the group consisting of lower alkoxy-carbonyl-methylene, lower-aryloxy-carbonyl-methylene, cyanomethylene, lower alkyl sulfinyl-methylene, lower alkyl sulfonyl-methylene, and $R_{25}$ and $R_{26}$ are independently selected from the group consisting of hydrogen, hydroxyl and lower alkyl.

1 Claim, No Drawings

STEREOSPECIFIC TOTAL STEROIDAL SYNTHESIS VIA SUBSTITUTED C/D-TRANS INDANONES

This is a division of application Ser. No. 482,711 filed June 24, 1974, now U.S. Pat. No. 3,984,474 which in turn is a division of application Ser. No. 765,023 filed Oct. 4, 1968 now U.S. Pat. No. 3,897,460.

BACKGROUND OF THE INVENTION

In recent years, much effort has been devoted to the total synthesis of steroids. The present invention relates to certain polycyclic compounds and processes for their synthesis. The novel intermediates and processes of this invention provide a new synthetic route for the preparation of pharmaceutically valuable steroids.

SUMMARY OF THE INVENTION

In one aspect, this invention relates to a process for preparing intermediates useful in the preparation of tricyclic compounds of the formula

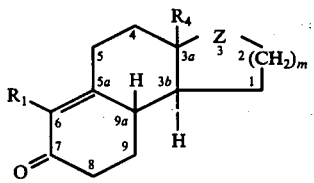

I wherein $R_1$ is hydrogen or lower alkyl; $R_4$ is hydrogen or lower alkyl; Z is defined hereinafter; m is an integer having the value of 1 or 2.

Another aspect of this invention relates to a process for preparing intermediates which enable the direct preparation of steroids of the formulae

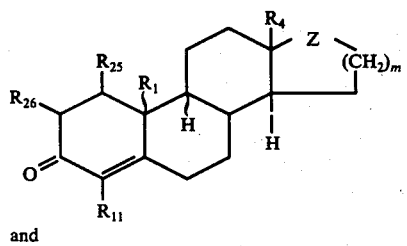

II and

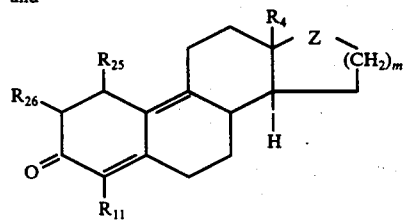

III wherein $R_1$, $R_4$ and m are as defined above; Z is defined hereinafter; $R_{11}$ is hydrogen or lower alkyl and $R_{25}$ and $R_{26}$ are independently selected from the group consisting of lower alkyl, hydrogen and hydroxyl.

In accordance with this invention, it has been discovered that compounds of the formulae I, II and III above, can be synthesized depending on the particular starting reactants selected by employing as intermediates bicyclic compounds of the formula

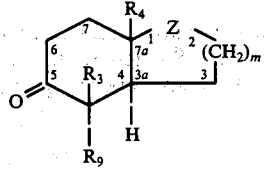

IV wherein m is an integer having a value of 1 or 2; $R_4$ is hydrogen or lower alkyl; Z is lower alkylenedioxy, $CH(OR_2)$ and carbonyl; $R_8$ when taken alone is hydrogen; $R_9$ when taken alone is lower alkoxy-carbonyl, aryloxy-carbonyl, lower cycloalkyloxy-carbonyl, carbonyl-halide, hydrogen, carboxy, formyl and methylene-X, where X is a leaving group and when taken together are methylene; with the proviso that when Z is carbonyl, $R_8$ when taken alone is hydrogen; $R_8$ when taken alone is carbonyl halide, hydrogen, carboxy, formyl and methylene-X where X is a leaving group and when taken together are methylene and $R_2$ is hydrogen, lower alkyl, lower alkoxy-lower alkyl, phenyl-lower alkyl, tetrahydropyranyl, lower alkanoyl, benzoyl, nitrobenzoyl, carboxy-lower alkanoyl, carboxy-benzoyl, trifluoroacety and camphorsulfonyl and reacting them in the care where $R_8$ and $R_9$ taken together are methylene or $R_8$ is hydrogen and $R_9$ is methylene-X with β-keto esters and other analogs of the formula

V $$R_6-\overset{O}{\underset{\|}{C}}-B$$

wherein $R_6$ is selected from the group consisting of

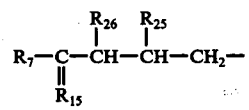

$$R_7-\underset{\underset{R_{15}}{\|}}{C}-CH\underset{R_{26}}{|}-CH\underset{R_{25}}{|}-CH_2-$$

and lower alkyl; $R_7$ is lower alkyl; $R_{15}$ is selected from the group consisting of oxo, lower alkylenedioxy or (hydrogen and lower alkoxy); B is selected from the group consisting of lower alkoxy-carbonyl-methylene, lower-aryloxy-carbonyl-methylene, cyanomethylene, lower alkyl sulfinyl-methylene, lower alkyl sulfonyl-methylene, and $R_{25}$ and $R_{26}$ are independently selected from the group consisting of hydrogen, hydroxyl and lower alkyl.

In still another aspect, this invention relates to the preparation of the compounds of formula III above wherein $R_{11}$ is hydrogen, by reacting the compounds of formulae IV-a and IV-c with a vinylogous cyclic-beta-keto compound of he formula:

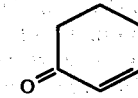

VI wherein B' is selected from the group consisting of lower alkoxy carbonyl-methylene, lower aryloxy carbonyl-methylene, lower alkyl sulfinyl-methylene and lower alkyl sulfonyl-methylene.

Structure III can also be obtained starting with a compound of the formula V, in which $R_{15}$ has been chosen to be oxo by reaction with compounds of the formulae IV-a and IV-c.

A further aspect of this invention relates to novel intermediates of the formula IV. Subgeneric to the bicyclic compound of formula IV above are compounds of the formulae:

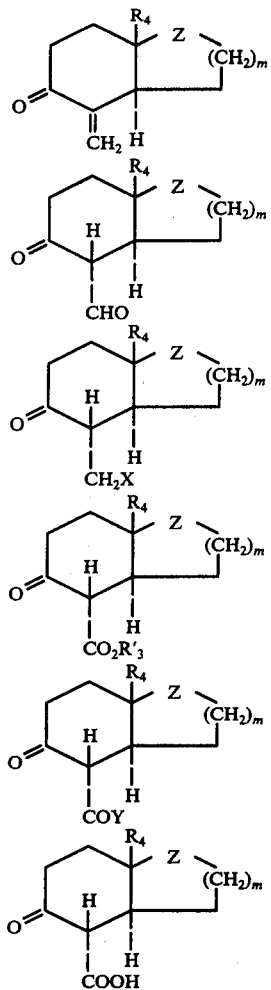

wherein $R_4$, Z, m and X are as defined aforesaid; Y is selected from the group consisting of fluorine, chlorine, bromine and iodine and $R'_3$ is selected from the group consisting of lower alkyl, lower cycloalkyl and aryl.

DETAILED DESCRIPTION OF THE INVENTION

In one aspect, this invention is concerned with novel indanones of the formulae IV, IV-a, IV-b, IV-c, IV-d, IV-e and IV-f which are useful as chemical intermediates as described herein. Also, certain of the keto compounds of formula V are novel and are also considered within the scope of this invention. For purposes of convenience, the rings in formulae I and IV have been numbered. Throughout this specification, in the formulae of compounds containing asymmetric centers or in the designation of such compounds by chemical nomenclature, the desired enantiomeric form is shown or designated. However, unless explicitly indicated otherwise, such illustration and designation should be taken as comprehending the enantiomer shown or designated, as well as its optical antipode or their corresponding racemate. In the formulae presented herein, the various substituents on cyclic compounds are joined to the cyclic nucleus by one of two notations, a solid line (—) indicating a substituent which is in the β-orientation (i.e., above the plane of the paper), or a dotted line (- - -) indicating a substituent which is in the α-orientation (below the plane of the paper).

As used herein, the term "lower alkyl" comprehends both side and branched chain hydrocarbon moieties such as methyl, ethyl, isopropyl, n-propyl, t-butyl and the like, having 1 to 7 carbon atoms in the chain. The preferred compounds are those derivatives wherein $R_4$ is methyl, ethyl and propyl which can be converted into steroids which exhibit exceptionally active pharmacological properties as hereinafter described. The formative "lower-alkyl" when used in expressions such as lower alkoxy-lower alkyl have the same significance. Thus, exemplary of the expression lower alkoxy-lower alkyl is α-ethoxy-ethyl and 3-propoxy-propyl. Exemplary of lower alkanoyl are acetyl and propionyl or other residues derived from lower alkane carboxylic acids of 1 to 6 carbon atoms; lower alkylenedioxy is understood to mean alkylene of 1 to 6 carbon atoms exemplary of which is ethylenedioxy. The term "nitrobenzoyl" as used herein comprehends benzo moieties containing one or more aromatic nitrile substituents, for example, nitrobenzoyl moieties such as 4-nitro-benzoyl and di-nitrobenzoyl moieties such as 3,5-dinitrobenzoyl. The expression carboxy-lower alkanoyl comprehends di-basic aliphatic acids of 1 to 7 carbon atoms absent one OH moiety. Similarly, the expression "carboxy-benzoyl" denotes, for example, phthalic acids absent one OH moiety. The expression "halide" or "halogen" comprehends chlorine, fluorine, bromine and iodine. The expression "lower alkoxy" as utilized herein designates a lower alkyl ether group such as methoxy, ethoxy and the like wherein the alkyl group is as defined above. The term "lower alkoxy carbonyl methylene" includes for example, ethoxy carbonyl-methylene. The term "lower aryloxy carbonyl methylene" includes for example, phenyloxy carbonyl methylene. The term "aryl" comprehends phenyl or phenyl having one or more substituents selected from the group consisting of lower alkyl, lower alkoxy, nitro, amine and halogen. The expression "lower alkylaryl" comprehends, for example, tolyl and ethylphenyl. The term cycloalkyl includes rings containing from 1 to 6 atoms, for example, cycloalkyl and cyclopentyl. Expecially preferred compounds of formula IV are those wherein "Z" is lower alkoxy, especially t-butoxy although the other derivatives defined hereinabove such as, tetrahydropyranyloxy can be suitably employed in accordance with the process of this invention.

The following schematic flow sheet entitled "Reaction Scheme A", exemplifies the process routes employed in accordance with the teachings of this invention for preparation via process routes (1), (2), (3), (4), (5), (6), (7), (8), (9) and (10), the key intermediates of the formulae IV-c and IV-a, each of which can independently be reacted with the β-keto esters and other analogs thereof of formula V to yield the end-products of formulae, I, II and III as hereinafter detailed.

Thus, in one aspect of the process of this invention, comprises preparing compounds of the formula IV-a by the general reaction steps (1), (2) and (4) of Reaction Scheme A to which the numerals and letters in parenthesis are referenced in the following descriptions.

Many of the indanone starting reactants of formula VII wherein "Z" is carbonyl are known. They may be conveniently synthesized by methods known in the art, for example, by the Michael Addition of methyl-vinyl-ketone to 2- lower alkyl-cyclopentane-1,3-dione. The cyclization can be effected using pyrrolidine in a benzene solvent under reflux reaction conditions (cf., U.S. Pat. No. 3,321,488). If desired, other derivatives of formula VII may be prepared. For example, in order to prepare the derivatives wherein Z is hydroxy, the corresponding oxo group can be selectively reduced with lithium aluminum tri-(lower alkoxy)-hydride or sodium borohydride at low temperatures. Derivatives wherein Z is lower alkoxy, for example, tertiarybutoxy, can be obtained from the corresponding hydroxy derivative by reaction under acid conditions with isobutylene by means known in the art. 1-Carboxy-lower alkanoyl derivatives of formula VII can be conveniently obtained by reacting dibasic lower alkanoic acids such as, succinic acid and phthalic acid and the like, with corresponding compounds containing the hydroxy-methylene moiety. Other derivatives in accordance with the definition of "Z" can be obtained by methods known to those skilled in the art.

REACTION SCHEME A

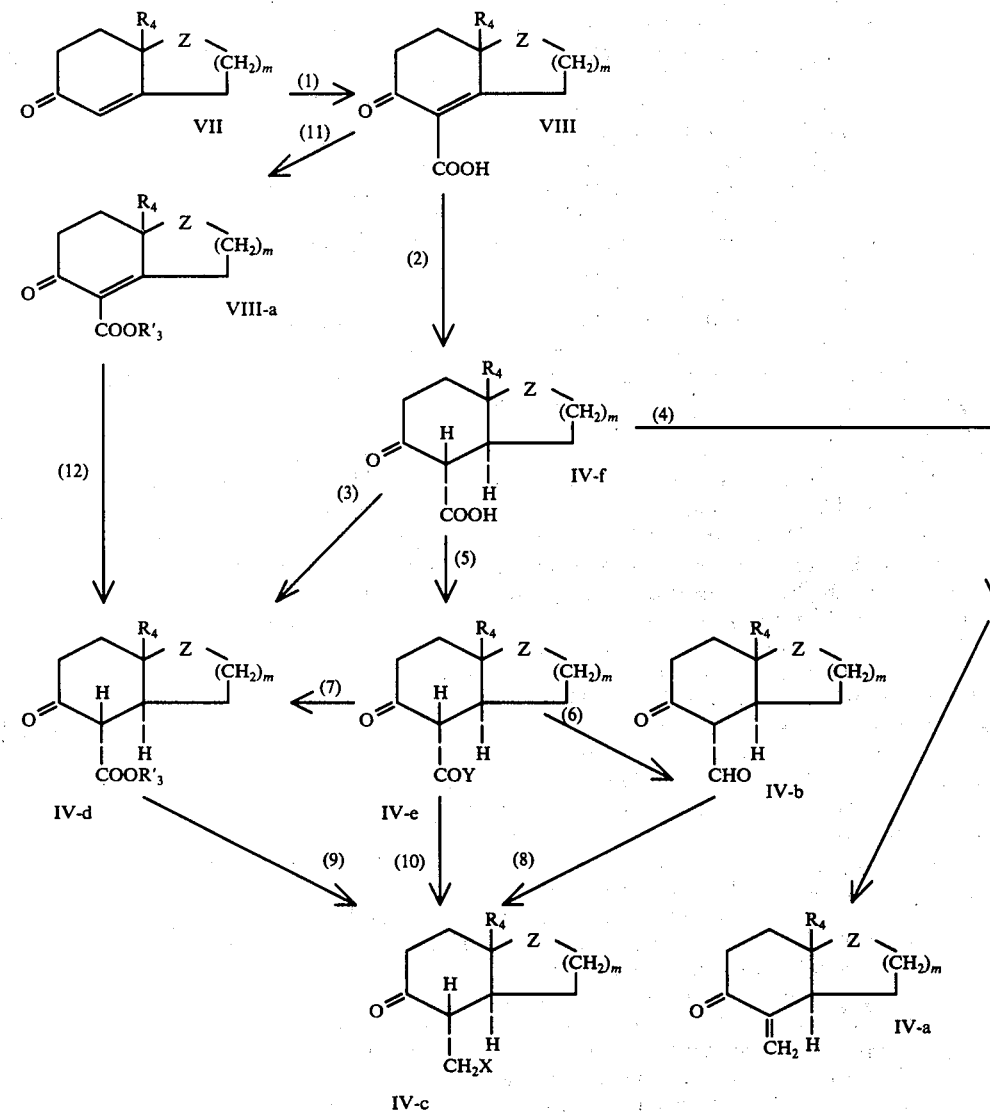

wherein $R_4$, Z, m, $R'_3$, X and Y are as defined aforesaid.

The bicyclic ketone of formula VII can be converted to acid compounds of formula VIII by reaction in accordance with Step (1) of Reaction Scheme A with a base sufficiently strong to afford the corresponding anion of the bicyclic compound via conjugate enolate formation. Exemplary of the suitable bases for this reaction are alkali metal amides such as sodium amide and the like; alkali metal alkoxides such as lithium methoxide and the like and alkali metal hydrides such as sodium hydride. Generally, it is preferred to conduct this reaction at room temperature although temperatures from about −40° C. to the boiling point of the reaction mixture can be utilized. The reaction is conveniently carried out in liquid ammonia or in the presence of an organic solvent inert to the reactants such as dimethylsulfoxide, dimethylformamide; hydrocarbons, e.g., benzene and toluene; and ethers, e.g., diethylether and tetrahydrofuran. A preferred solvent for this reaction is dimethylsulfoxide. This intermediate enolate bicyclic reaction product can be isolated by conventional techniques such as, for example, by removal of the solvent using vacuum distillation.

The anion which is thus obtained as a residue can be carboxylated by reaction with excess carbon dioxide to afford the 4-indane carbocyclic acid of the formula VIII. The carboxylation can be suitably effected by employing solid carbon dioxide in the form of dry ice or passing gaseous carbon dioxide into the reaction medium. Exemplary of the desirable solvents for this reaction are any of the aforementioned listed solvents which can be employed to prepare the anion with the exception of liquid ammonia, which is basic and dimethylsulfoxide, which tends to promote decarboxylation. In cases wherein liquid ammonia or dimethylsulfoxide is employed to prepare the anion, an inert solvent should be substituted when conducting the carbonation reaction. Suitable reaction temperatures are in the range of −60° C and about 40° C. A preferred operating temperature range is 15° C–25° C. Separation of the desired reaction product from the reaction medium can be effected by extraction. the extraction is suitably conducted in a hydrocarbon solvent in the presence of a dilute base such as sodium hydroxide or lithium carbonate to form the corresponding water soluble salt of the acid. Base extraction is employed so as to remove the desired product from the starting material. The aqueous layer is separated and carefully acidified to a pH of between 2.5 and 4.5 with dilute mineral acid and the desired product is then obtained by conventional techniques. Although the reaction can be suitably conducted at atmospheric pressure, increased yields can be obtained by conducting the reaction under higher pressures, e.g., in the range of 450 to 550 psi. Carboxylation takes place only at C-4 position on the indane nucleus in agreement with the preference for heteroannular conjugate anion formation with compound VII.

Inasmuch as the ultimate goal of this invention is to produce a compound of the formula I containing a 9α-configuration, it is clear that the hydrogenation of the compound of formula VIII in accordance with Step (2) of Reaction Scheme A must predominantly proceed so as to yield a trans-hydrogenation product with respect to the two rings of the 5-indanone or the corresponding 2-napthalenone compounds. A feature of this invention is that the desired hydrogenation to yield a transfused bicyclic structure can be effected in extremely high yields. The hydrogenation is conducted in the presence of a catalyst preferably a noble metal catalyst, such as palladium, rhodium, irridium, platinum and the like. Especially preferred is the palladium catalyst. The noble metal catalyst can be utilized with or without a carrier and if a carrier is used, conventional carriers are suitable. It is preferred to use palladium on barium or calcium sulfate. Especially preferred is 10 percent Pd/BaSO$_4$. The ratio of catalyst to substrate is not critical and can be varied. However, it has been found advantageous to use a weight ratio of catalyst to substrate from about 1:1 to about 1:10. Especially preferred is a ratio of 1:3. The hydrogenation is suitably effected in the presence of an inert organic solvent for the particular compound of formula VII being hydrogenated, for example, a lower alkanol, such as methanol, isopropanol or octanol; ketones for example, lower alkyl ketones such as acetone or methylethyl ketone; lower alkyl esters of lower alkanoic acids such as ethyl acetate; lower alkyl ethers such as diethyl ether to tetrahydrofuran; aromatic hydrocarbons such as toluene or benzene and the like. It is especially preferred to conduct the hydrogenation using a lower alkanol as the solvent and it is preferably conducted under non-acidic conditions. Suitably, the hydrogenation is conducted under neutral conditions. It can be conducted at atmospheric pressure or below or above atmospheric pressure, for example, at pressures of as high as about 50 atmosphere. Also, the hydrogenation can be conducted at room temperature or temperatures above or below room temperature. As a matter of convenience, it is preferred to conduct the hydrogenation at room temperature. The hydrogenation is effected by utilizing conventional techniques, for example, the hydrogenation should be stopped after the uptake of the equivalent of hydrogen or if the absorption of hydrogen ceases before the uptake of an equivalent of hydrogen, it is advantageous to then add more catalyst and further hydrogenate. It will be appreciated that another significant aspect of this hydrogenation step lies in that the hydrogenation of the compound of formula VIII to afford the compound of formula IV-f proceeds without substantial decarboxylation of the substituted indane of formula VIII. Depending on the hydrogenation conditions used, the group represented by "Z" in formula VIII can be modified during the hydrogenation. For example, under the above-described hydrogenation conditions, when Z is OR$_2$ and R$_2$ is a group such as alkoxy-lower alkyl or tetrahydropyranyl, such group can be split off during the hydrogenation procedure. A preferred group for R$_2$ in which to conduct the hydrogenation and many of the subsequent other reactions is alkyl, especially, t-butyl.

The thus obtained saturated compound of formula IV-f can be converted to the 4-methylene-trans-fused compounds of formula IV-a by employing a modified Mannich-type reaction in accordance with Step (4) of Reaction Scheme A. The conversion can be effected using formaldehyde in the presence of a primary or secondary amine salts. Suitable salts which may be employed are those derived from strong mineral or organic acids such as for example, hydrogen halides, preferably as the chloride, sulfuric acid, oxalic acid and the like, such as for example, piperidine hydrochloride. The reaction can be suitably carried out at a temperature range of from 0° C to about 80° C. A preferred temperature range for this reaction is 15° C–40° C. While the ratio of reactants used for the reaction is not critical, it has been found advantageous to use approximately a 10:1 molar ratio of formaldehyde to keto acid and a 0.1:1 to 1:1 molar ratio of amine to keto acid.

The reaction is best effected in a dimethylsulfoxide solvent which functions both as a solvent for the reaction and also as a decarboxylating agent. Most advantageous results are obtained by allowing the compound of formula IV-f to decarboxylate in the dimethylsulfoxide solvent so as to form the corresponding anion and quench it immediately with the Mannich System formed by the addition of formaldehyde and primary or secondary amine salt. Aqueous formalin (37 percent − 40 percent) is a generally satisfactory source of formaldehyde for this reaction. Exemplary of the amines suitable for this reaction include heterocyclic amines such as morpholine, piperidine and pyrrolidine; monoamines such as methylamine, butylamine and benzylamine. An especially preferred amine for this reaction is piperidine. Other polar solvents such as, for example, dimethylformamide and hexamethylphosphoramide which are inert to the reactants may be employed in conjunction with the dimethylsulfoxide. The dimethylsulfoxide solvent promotes decarboxylation and anion formation at the bicyclic C-4 position notwithstanding the known preferential tendency of these compounds to enolize in the direction of the bicyclic C-6 position.

In another aspect of this invention in accordance with Reaction Scheme A, compounds of Formula IV-c may be prepared by alternate process routes (3→9), (5→7→9), (5→10) and (5→6→8).

Thus, the compounds of formula IV-e can be prepared in accordance with Step (5) from the β-keto acids of formula IV-f in excellent yields employing an organic or inorganic acyl halide preferably thionyl halide, e.g., thionyl chloride; phosphorous trihalide, preferably phosphorous trichloride and phosphorous pentahalide, preferably phosphorous pentachloride. Thionyl chloride is particularly convenient since the by-products formed are gases and can be easily separated from the acid chloride. Any excess of the low boiling thionyl chloride can be easily removed by distillation. This substitution reaction was successfully effected notwithstanding the known prior art [cf., C. B. Hurd et al., J. Am. Chem. Soc. 62, 1548, (1940)] which teaches the inability to prepare β-keto acyl halides by conventional reaction techniques from the corresponding β-keto acids. The reaction is suitably conducted at a temperature of from 0° C to the boiling point of the solvent. Suitable solvents for the conversion are thionyl chloride (neat) or in an inert organic solvent such as, for example, benzene, toluene, hexane, cyclohexane and the like.

4-Carbonyl halide indanone compounds of formula IV-e, can be converted to the corresponding esters of formula IV-d by means known in the art. Preferred esters are those wherein $R'_3$ is lower alkyl, especially methyl and ethyl. The esters can be conveniently obtained by reacting the halide with an alkali alkoxide, e.g., sodium methoxide in a solvent such as, for example, lower alcohol, e.g., methanol and the like. Alternatively, the esters of formula IV-d may be obtained by reacting the halide with carbonyl diimidazolide in tetrahydrofuran solvent, then further reacting the thus obtained product with the desired aliphatic or aryl alcohol, e.g., phenol, methanol, ethanol and the like at room temperature to the reflux temperature of the solvent in, for example, tetrahydrofuran to obtain the desired ester.

As a further alternate wherein it is desired to prepare 4-alkoxy carbonyl indanones of formula IV-d, the conversion can be effected by treatment of the acids of formula IV-f with an ethereal solution of a diazoalkane such as diazomethane by known means. The reagent is a yellow gas and small quantities can be prepared conveniently prior to use in the form of a solution in ether. When the yellow ethereal solution is added in portions to a solution or suspension of the acid in ether at room temperature, nitrogen is evolved at once and the yellow color is discharged. When the yellow color persists, which is an indication that excess diazomethane has been added, the solution can be heated, e.g., on a steam bath to expel excess reagent. Since the only by-product is a gas, a solution of the desired ester in ether results.

The esters of formula IV-d can also be prepared by first esterifying the unsaturated acid compounds of formula VIII to compounds of formula VIII-a in accordance with Reaction Scheme A by the aforementioned methods and then catalytically hydrogenating this unsaturated ester. The steric course of this hydrogenation proceeds so as to yield the C/D-trans-hydrogenated product. Thus, an identical product of the structure of formula IV-d with C/D-trans-ring fusion is obtained in a similar manner to the case wherein the acid of formula VIII is employed directly as the starting reactant for the hydrogenation step. The bicyclic C/D-trans-structure obtained by the catalytic hydrogenation of the ester may be explained (although applicant is not bound by this theory) by postulating a chelated dienol ester intermediate formed from the non-enolic unsaturated β-keto ester on the surface of the catalyst. However, it should be noted that the rate of catalytic hydrogenation of the β-keto acid of formula VIII was approximately four times as rapid as was the case when the corresponding β-keto ester was employed as the reactant. However, hydrogenation of the ester employing approximately three times the amount of catalyst employed in the case of the acid under identical reaction conditions resulted in an approximately equal hydrogenation rate.

The β-keto aldehydes of formula IV-b can be prepared from the acid halides of formula IV-c in accordance with Step (6) of Reaction Scheme A employing a reducing agent such as, lithium aluminum tritertiarybutoxyhydride. The reaction can be carried out in an inert aprotic organic solvent such as, ethers, e.g., tetrahydrofuran and hydrocarbons, e.g., toluene and hexane at a temperature range of −10° C. to −60° C., preferably between the temperature range of −20° C. and −40° C. When the reaction is carried out within the aforesaid defined temperature ranges, selective reduction of the acid halide can be effected without attacking the free keto group on the 5-positon of the indane of formula IV-e. An alternative method of transforming the acid halide to the corresponding aldehydes can be accomplished by the catalytic hydrogenation of the acid chloride by the Rosenmund Reaction. The technique introduced by Rosenmund consists in adding a small amount of a poisoning agent containing sulfur to the hydrogen catalyst system.

The indanones of formula IV-e wherein $R_4$, Z and m are as defined as aforesaid can be conveniently prepared in accordance with Steps (8), (9) and (10) of Reaction Scheme A depending upon the nature of "X", from the esters of formula IV-d, the acid halides of formula IV-e or the aldehydes of formula IV-b.

Suitable requirements for the leaving group as defined by "X" in the compounds of formula IV-e are that it should function efficaciously in this process aspect, that is, that it be a suitable leaving group for the process of the present invention. Suitable groups which may be employed to form leaving groups are lower alkyl-aryl sulfonyloxy groups such as, for example, tosyloxy; arylsulfonyloxy groups such as, for example, benzene sulfonyloxy; lower alkyl sulfonyloxy groups such as, for example, mesyloxy (methane sulfonyl); lower alkyl sulfinyloxy; halogen; an acyloxy radical derived from an organic carboxylic acid having 1 to 7 carbon atoms such as lower alkanoic acid, e.g., acetic acid and butyric acid; aryl carboxylic acids such as p-phenylbenzoic acid and benzoic acid and cycloalkyl carboxylic acids such as cyclopantyl carboxylic acids. Other suitable leaving groups may be selected from the group consisting of

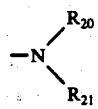

wherein each of $R_{20}$ and $R_{21}$ is independently selected from the group consisting of lower alkyl, aryl and hydrogen, and $R_{20}$ and $R_{21}$ when taken together to the nitrogen atom to which they are joined, form a 5- or 6-membered heterocyclic ring structure. Thus, the

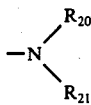

amino grouping represents secondary and tertiaryamino radicals. It includes monoalkylamino radicals, such as, for example, methyleneamino and butylamino; dialkylamino radicals such as, for example, dimethylamino and dipropylamino, heterocyclic amino radicals, such as, for example, pyrolidino, piperidino, morphelino and 4-methyl-piperizino. The amino radical

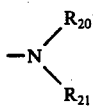

may also be employed as a leaving group in a modified form by alkylation by known means with a suitable organic ester such as, for example, lower alkyl halide, e.g., methyl chloride or a hydrohalic acid such as, for example, hydrogen chloride to form the corresponding quaternary ammonium salt of the formula

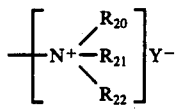

wherein $R_{20}$, $R_{21}$ and Y are as defined aforesaid and $R_{22}$ is a cation from the organic ester.

Generically, the preferred leaving groups are tosyloxy and mesyloxy although depending on the steroidal end products being prepared, other leaving groups as exemplified above may be more preferable.

The compounds of formula IV-c wherein the leaving group "X" is lower alkyl-sulfonyloxy, e.g., mesyloxy or lower alkyl aryl-sulfonyloxy, e.g., tosyloxy may be conveniently prepared from the esters of formula IV-d in accordance with Step (9) of Reaction Scheme A by a reaction sequence which comprises first protecting the 5-oxo moiety on the indanone, reducing the ester group to the corresponding 4-hydroxy methylene derivative, removing the protecting group before or after conversion to the desired derivative of formula IV-c. Protection can be effected by converting the free oxo group to a cyclic ketal, e.g., a dioxolane ring system by reaction with a suitable lower alkylenedioxy containing compound, e.g., ethylene glycol or to an open ketal with for example, tri-lower alkyl orthofermates. The free oxo moiety can be regenerated after reduction of the 4-ester compounds of formula IV-d to the corresponding 4-hydroxy methylene compounds. A preferred protecting group is the dimethoxy derivative which can suitably be obtained by etherification with trimethyl orthoformate. The thus protected 4α-ester can be reduced employing for example, a suitable reducing agent such as, diisobutyl aluminum hydride to yield the 4-hydroxy methylene compound of the formula

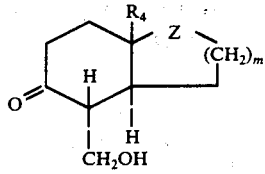

wherein $R_4$, Z and m are as defined aforesaid.

Alternatively, the ester of formula IV-d in the protected form obtained as described above may be reduced to the alcohol of formula IV-c-1 using an alkali metal reducing agent such as sodium metal and lower alcohol or lithium aluminum hydride. Compounds of formula IV-c wherein the leaving group "X" is lower alkyl sulfonyloxy or lower alkyl-arylsulfonyloxy can be prepared by esterification with an organic sulfonylhalide such as, for example, toluenesulfonyl halide, especially, p-toluenesulfonyl chloride to prepare the tosyloxy derivative or lower alkyl sulfonyl halides, especially methane sulfonyl chloride to prepare the mesyloxy derivative. The above reactions can be suitably conducted at a temperature range of $-10°$ C to $+10°$ C in the presence of an organic base such as, for example, pyridine by methods known in the art. The corresponding sulfonic acids may also suitably be employed to effect the esterification in lieu of the sulfonyl halide. Leaving groups wherein "X" is lower alkyl sulfinyloxy may be obtained in an analogous manner to that above by employing the corresponding sulfinyl halides.

Leaving groups wherein "X" is defined by the grouping

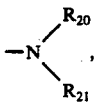

wherein $R_{20}$ and $R_{21}$ are defined as aforesaid can be conveniently obtained from the acid halides of formula IV-e in accordance with process route (10) of Reaction Scheme A by a reaction sequence which comprises the steps of (a) reacting the compounds of formula IV-e with a primary or secondary aliphatic or aromatic amine of the formula

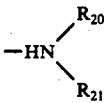

by known means to form the corresponding amide of the formula

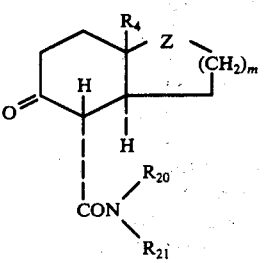

wherein $R_4$, Z, m and $R_{20}$ and $R_{21}$ are as defined aforesaid;

(b) protecting the 5-oxo group of the compounds of formula IV-c-2 by forming the 5-ketal analog in a manner similar to that previously described; (c) reducing the amide with a suitable reducing agent such as, for example, diborane or lithium aluminum hydride in an ether solvent such as, for example, tetrahydrofuran which upon removal of the protecting group by means of dilute mineral acid yields a compound of the formula:

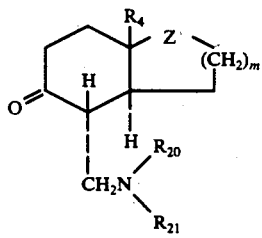

IV-c-3 wherein $R_4$, Z, m, $R_{20}$ and $R_{21}$ are as defined aforesaid. The compounds of formula IV-c-3 can be converted to their quaternary salt adducts by alkylation with for example, a lower alkyl halide such as methyl chloride.

Leaving groups wherein "X" is defined by the grouping

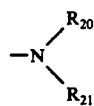

wherein at least either $R_{20}$ and $R_{21}$ is hydrogen, may also be prepared from the aldehydes of formula IV-b in accordance with process route (8) of Reaction Scheme A by selective condensation with a primary amine of the formula $-H_2NR_{20}$ to form by known means the novel imino Shiff Base intermediate of the formula

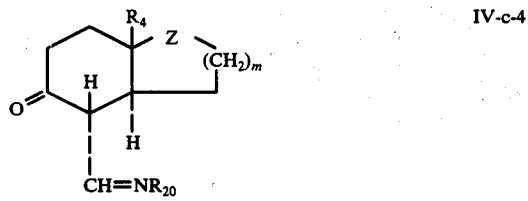

wherein $R_4$, Z, m and $R_{20}$ are as defined aforesaid.

The ald-imines of formula IV-c-4 can be conveniently reduced with hydrogen and Raney Nickel to the desired secondary amines.

Leaving groups wherein "X" is defined as halogen may be conveniently obtained from the alcohols of formula IV-c-1 by reaction with for example, hydrogen halides, e.g., hydrogen chloride, phosphorous halides or thionyl chloride by means known in the art. Leaving groups wherein "X" is acyloxy as defined aforesaid may be suitably obtained from the compounds of formula IV-c-1 by reaction with the desired organic carboxylic acid in the presence of a mineral acid such as sulfuric acid or hydrochloric acid at reflux temperature by means known in the art.

In another aspect, the process of this invention relates to the preparation of compounds of the formulae I, II and III by reaction of a β-keto ester or other analog of formula V with compounds of formulae IV-c and IV-a in accordance with Reaction Scheme B. It should be appreciated that compounds of the formulae IV-a and IV-c can be used interchangeably in all of the hereinafter process reactions.

REACTION SCHEME B

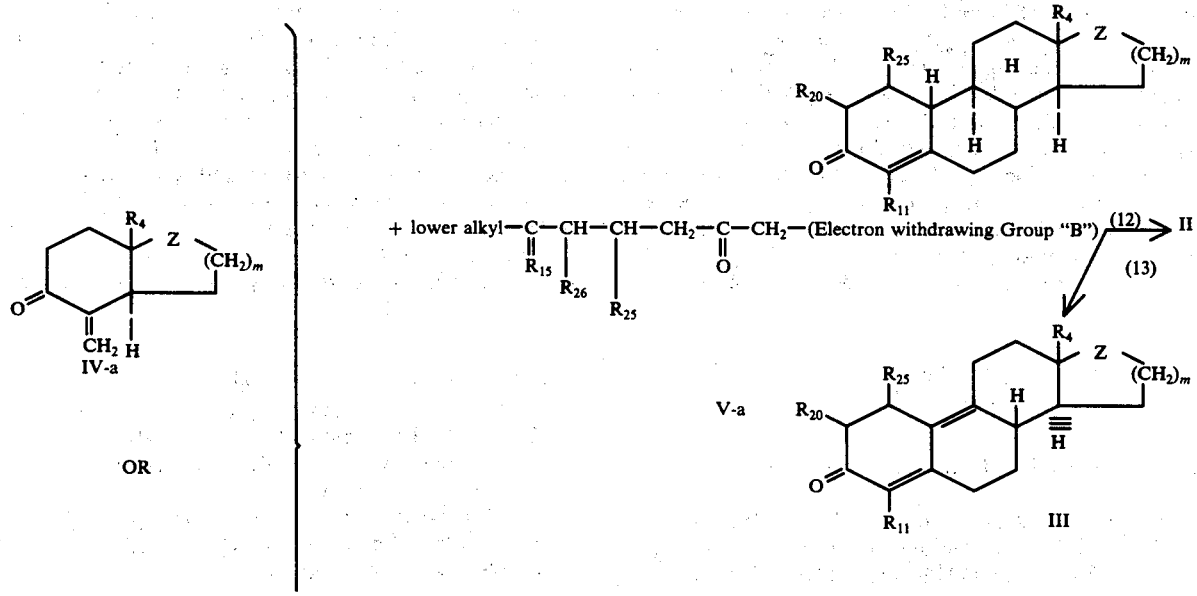

-continued
REACTION SCHEME B

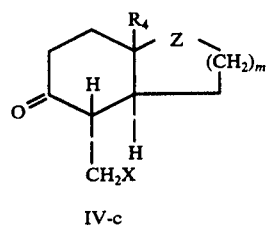

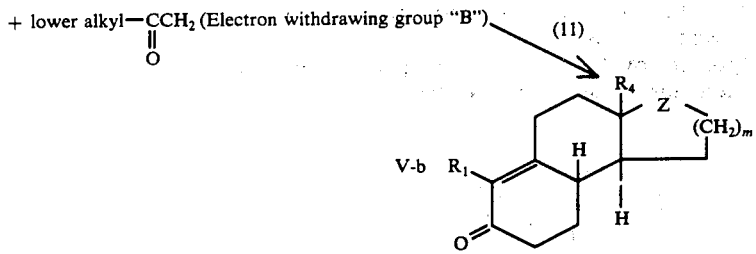

wherein $R_4$, m, X, Z, $R_{25}$, $R_{26}$, $R_{11}$ and $R_1$ are as defined aforesaid. (See Reaction Scheme D)

The process of this invention in this aspect, comprises employing the bicyclic indanone derivatives of formulae I V-a and IV-c prepared as aforesaid and reacting them with certain subgeneric compounds encompassed by generic compounds of the formula V-b in accordance with process route (11) of Reaction Scheme B to prepare the benz[e]indene compounds of formula I. Alternatively, for other subgeneric compounds encompassed by generic formula V-a in accordance with process routes (12) and (13) of Reaction Scheme B, the steroids of formulae II and III may be prepared. Thus, for certain compounds subgeneric to formula V, viz — formula V-b as defined below, the tricyclic benz[e]indenes of formula I may be prepared by means of the building in an annulation reaction steroidal ring B. Alternatively, for certain other compounds subgeneric to formula V-a as defined hereinafter, the steroids of formulae II and III may be prepared by building by means of compounds of formula V-a, steroidal rings A and B. Thus, the keto compounds of formula V are employed as one of the starting reactants for the preparation of the tricyclic compounds of the formula I or the tetracyclic compounds of formulae II and III. However, it will be appreciated that the length of the carbon chain varies as exemplified by formulae V-a and V-b below, depending on which class of end products are sought to be prepared. Thus, the β-keto esters and analogs thereof of formula V-a below, are employed wherein it is desired to prepare the tetracyclic steroids of formulae II and III.

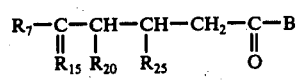 V-a wherein $R_7$, $R_{15}$, B, $R_{25}$ and $R_{26}$ are defined as aforesaid.

The β-keto esters and other analogs of formula V-a can be prepared in accordance with Reaction Scheme C below in which a specific embodiment is illustrated.

The β-keto esters of formula V-a-1 can be prepared from the hexanoic esters of formula X via process route (a) by reaction with base, preferably, lithium hydroxide in a lower alcohol solvent, e.g., ethyl alcohol at the reflux temperature of the solvent to form the salt of the acid by saponification of the ester. Subsequent reaction of the thus obtained salt with equimolar quantity of an organo metallic compound, preferably, methyl lithium in tetrahydrofuran in the presence of a minute amount of triphenylmethane yields the compounds of formula XII. In effecting the conversion, $R_{15}$ should be in a protected keto form, e.g., ketal, the conversion to which has been herein before described. Alternatively, the compounds of formula XII can be prepared in accordance with Reaction Scheme C, via process routes (b) and (c) by reacting the compounds of formula X with a lower alkyl sulfinyl methylene compound, e.g., methyl sulfinyl carbanion [cf., E. J. Corey and M. Chaykovsky, J. Am. Chem. Soc. 86, 1639 (1964)] to yield intermediates of formula XI. The compounds of formula XI can if desired, be oxidized to the sulfonyl derivatives with an oxidizing agent such as, for example, potassium permanganate. Reduction of the thus obtained sulfoxides of formula XI with a reducing agent, preferably, aluminum amalgam, yields compounds of formula XII. The compounds of formula XII can be converted to the β-keto esters of formula V-a-1 via a Claisen Condensation with a carbonate of the formula $$(R_5)_2CO_3$$

wherein $R_5$ is aryl or lower alkyl in accordance with process route (e). The preferred condensing agent is sodium hydride although alkali lower alkoxides, e.g., sodium alkoxide may also be suitably employed. The reaction is conveniently conducted in an ether solvent such as, for example, diethylether or tetrahydrofuran, the former being preferred at the reflux temperature of the solvent.

REACTION SCHEME C

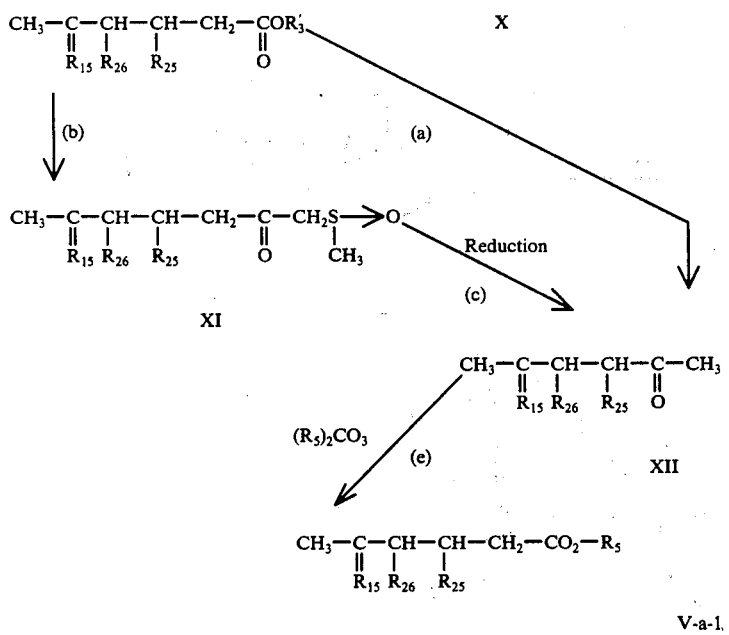

wherein $R_{15}$, $R_{25}$, $R_{26}$, and $R'_3$ are defined as aforesaid and $R_5$ is lower alkyl or aryl.

Illustrative of the $\beta$-keto ester and other analog compounds of formula V-a which may be employed as starting reactants wherein it is desired to prepare the steroids of formulae II or III include 6-(2-methyl-1,3-dioxolan-2-yl)-3-oxohexanoic acid ethyl ester; 6-(2-ethyl-1,3-dioxolan-2-yl)-3-oxohexanoic acid ethyl ester; 3,7-dioxo-octanoic acid methyl ester; 6-(2-methyl-1,3-dioxolan-2-yl)-3-oxohexanoic acid propyl ester; 3,7-dioxodecanoic acid ethyl ester; 1-methylsulfinyl-5-(2-methyl-1,3-dioxolan-2-yl)-2-pentanone and the like. By referring to the general formula IV, it can be thus appreciated that when it is desired to prepare the steroids of formula XVII, the selections of the variables of formula V should be as follows: $R_6$ is

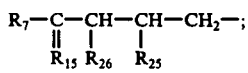

and $R_{25}$, $R_{26}$, $R_{15}$ and B are defined aforesaid.

The $\beta$-keto esters and other analogs of formula V-b below, are employed wherein it is desired to prepare the tricyclic compounds of formula I

      V-b wherein $R_6$ and B are defined as aforesaid.

The compounds of formula V-b, for example, ethyl propionyl acetate, may be prepared in a similar manner to the compounds of formula V-a in accordance with process step (e) by employing in Reaction Scheme C (the Claisen Condensation Step) butanone in lieu of the compounds of formula XII.

Exemplary of the $\beta$-keto ester and other analogs of formula V-b which may be employed as starting reactants wherein it is desired to prepare the tricyclic compounds of formula I include ethyl propionyl acetate, methyl propionyl acetate, ethyl aceto acetate, ethyl butyro acetate, butyro acetonitrile, acetoacetonitrile, 1-methyl-sulfinyl-2-butanone and 1-methyl-sulfonyl-2-pentanone.

While certain groups exemplified by the definition of the term "B" have been illustrated in the $\beta$-keto ester and other analogs of formulae V-a and V-b, it is to be understood that any other equivalent electron withdrawing group or groups of electrophilic nature can function as well. All that is required for the "B" segments of the molecule for the process of the reaction of the compounds of formula IV with the compounds of formula V is that it function efficaciously in this process aspect, that is, that it be a suitable electron withdrawing group so as to activate the hydrogen atom on the methylene group next adjacent to the carbonyl group. Preferred electron withdrawing groups are the alkoxy carbonyl esters, especially ethoxy carbonyl. The $\beta$-keto nitriles, e.g., aceto-acetonitrile of formula IV-b may be prepared by reaction of acetonitrile phenyllithium and diethylamine at a temperature range of $-10°$ C to $+10°$ C and hydrolyzing in dilute acid the thus obtained imine intermediate to the desired product [cf., Ann. 504, 94 (1933)]. The compounds of formula V-a and V-b wherein "B" is defined as lower alkyl sulfinyl methylene and lower alkyl sulfonyl methylene can be readily prepared from the esters of formula V-a-1 in a similar manner to that employed in process step (b) of Reaction Scheme C.

In a further aspect, the synthesis of the present invention relates to the preparation of steroids of the formulae II and III in accordance with Reaction Scheme B by means of reacting a carbon chain of the formula V-a with a bicyclic compound of the formulae IV-a or IV-c. In Reaction Scheme D, the numbers are assigned to Roman numerals for identification. Schematically, the sequence of reactions involved in the synthesis of a specific embodiment, namely, 19-nortestosterone is illustrated.

REACTION SCHEME D

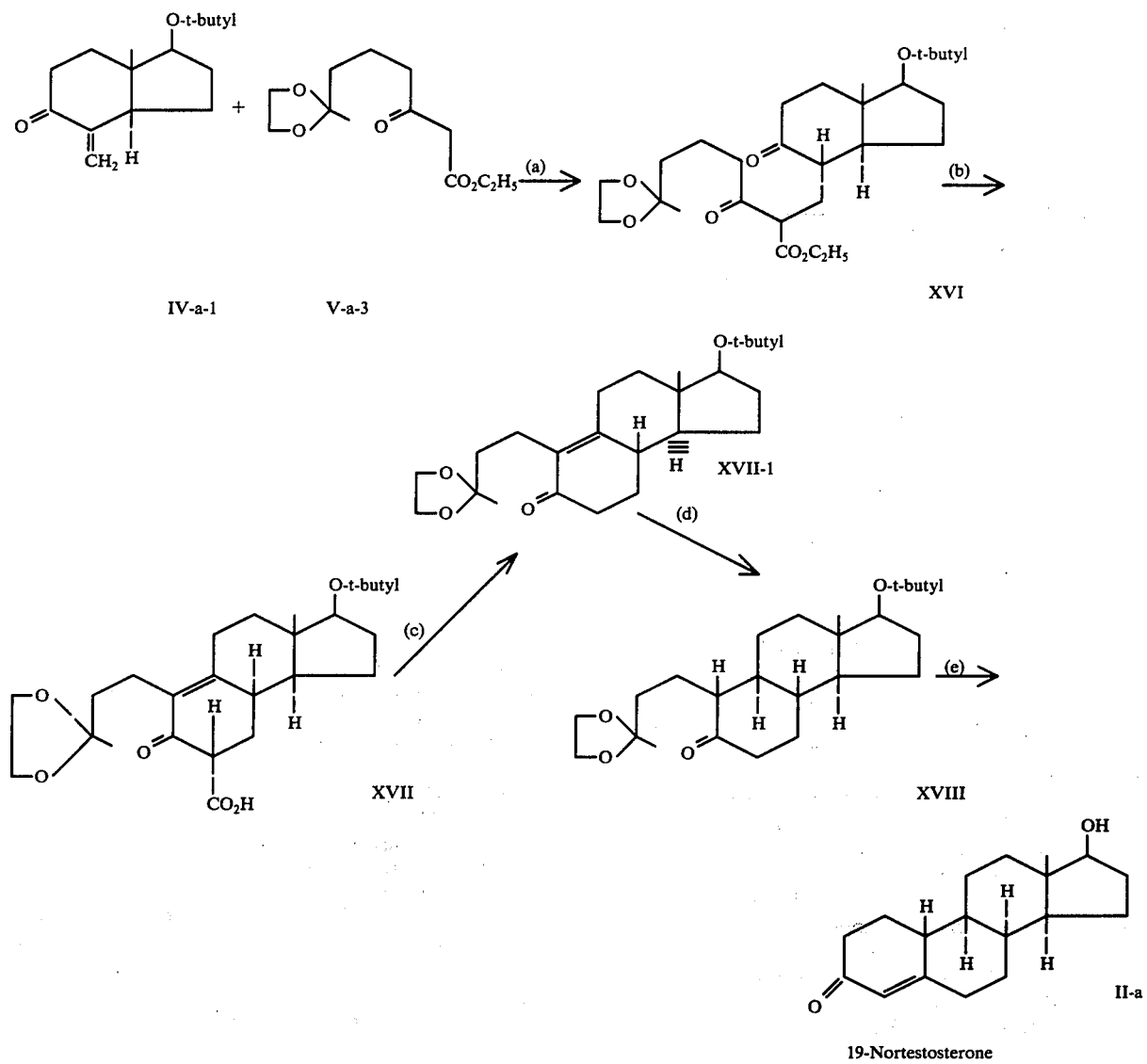

19-Nortestosterone

In the Michael addition, process step (a) of Reaction Scheme D, the precursors to the steroidal A and B rings are build up in a single annulation reaction. The reaction is conducted in the presence of a base sufficiently strong to form the anion of the β-keto ester. Exemplary bases are for example, alkali metal lower alkoxides such as sodium methoxide, sodium ethoxide, potassium methoxide, potassium tertiary butoxide and the like; alkali metal hydroxides such as sodium hydroxide and the like; alkali metal hydrides such as sodium hydride, lithium hydride and the like; alkali metal amides such as lithium amide, sodium amide and the like; methyl sulfinyl carbanion (i.e., the anion from dimethyl sulfoxide). Especially preferred are the alkali metal lower alkoxides. The reaction can be conducted at a temperature range of from about −5° C to about 100° C. However, it is especially advantageous to conduct a reaction within a temperature range of from 0° C to 25° C. Moreover, the reaction is suitably conducted in the absence of oxygen for example, in an atmosphere of inert gas such as nitrogen or argon. It is convenient to conduct the reaction in the presence of an organic solvent inert to the reactants as well as the intermediates of formula XVI. Such solvents are for example, dimethylformamide, dimethylsulfoxide and aromatic hydrocarbons, such as, for example, benzene, toluene and xylene. Other suitable solvents include the ethers such as diethylether, tetrahydrofuran and the like and lower alkanols such as methanol, ethanol and the like. The concentration of reactants is not critical but it is preferred to use a 1:1 molar ratio of reactants of formulae IV-a-1 and V-a-3. One may add the reactant of formula V-a-3 to a reaction mixture already containing the bicyclic indanone of formula IV-a-1. However, the reaction can also be effected by placing all the reactants substantially together or preferentially the reactants of formula IV-a-1 can be added to a mixture containing the reactants of formula V-a-3. When employing as a starting reactant, the compounds of formula IV-a in lieu of the reactants of formula IV-c-1, the same process conditions are employed and products obtained although the reaction does not necessarily have to proceed by way of a Michael addition mechanism. The sidechain of the reaction intermediate XVI assumes the thermodynamically favorable equatorial configuration under the equilibrating reaction conditions. The alpha orientation of the sidechain is extremely important for the construction of ring B with the proper stereochemistry. No ring closure occured at this stage because of the preferred enolization of the keto group towards the ester function. Following the Michael addition of the β-keto ester of formula V-a-3 to the bicyclic C/D-trans-indanone of formula IV-b-1, the thus obtained compound of formula XVI is saponified to remove the ester group and cyclized in accordance with process step (b) of Reaction Scheme D. The cyclization should be effected under reaction conditions which do not cleave the cyclic ketal protecting group. Exemplary basic cyclization reagents are for example, a dilute aqueous solution of alkali or alkaline metal hydroxides such as for example, sodium hydroxide, lithium hydroxide, calcium hydroxide and the like. The cyclization is suitably conducted in an inert organic solvent such as for example, hydrocarbons, e.g., benzene, toluene and ethers, e.g., tetrahydrofuran. The cyclization can be conducted at room temperature or above room temperature but as a matter of convenience, it is preferable to conduct the reaction at about room temperature. The ester group of the bicyclic intermediate of formula XVI can be removed by saponification of the ester in accordance with Step (b) of Reaction Scheme D to afford the corresponding acid of the formula XVII (after acidification) and decarboxylation to compounds of the formula XVII-1 for example, in refluxing toluene under an inert atmosphere such as for example, nitrogen in accordance with Step (c) of Reaction Scheme D. For other cases wherein the electron withdrawing group of formula V ("B") is other than ester, e.g., for example, lower alkyl sulfinyl methylene or lower alkyl sulfonyl methylene, the removal of the grouping can be effected by reduction with a reducing agent such as, for example, aluminum amalgam. For cases wherein the electron withdrawing group is nitrile, the reaction can be suitably conducted in an analogous manner to that wherein the electron withdrawing group is an ester as discussed above.

The hydrogenation of the $\Delta^{9(10)}$-double bond of the compounds of formula XVII-a to the compounds of formula XVIII can be effected in accordance with Step (d) of Reaction Scheme D in a lower alcohol solvent such as, for example, ethyl alcohol in the presence of a base, preferably, triethylamine. 19-Nortestosterone can be obtained from the compounds of formula XVIII by hydrolysis of the tertiarybutyl ether cyclization by refluxing in a mineral acid such as, hydrochloric acid or sulfuric acid in a lower alkanol solvent such as methanol in accordance with Step (e) of Reaction Scheme D.

It should be noted that the process steps exemplified in Reaction Scheme D can be utilized to prepare norgestrel. This can be effected by preparing the 7aβ-ethyl analogs of formula IV-a-1 as described on page 9 of the instant specification employing the reaction steps (a), (b), (c), (d) and (e) of Reaction Scheme D followed by oxidation utilizing for example, Jones Reagent and ethinylation in accordance with procedures described on page 49 of the instant application. It will be further appreciated that by employing the optically active 7aβ-ethylenantiomer of formula IV-a-1 of Reaction Scheme D, one can prepare optically active norgestrel.

It will be appreciated that this aspect of the process of the invention for the synthesis of steroids of the formula II of which 19-nortestosterone is a specific exemplar as set forth in Reaction Scheme D, can be modified so as to yield other pharmaceutically valuable steroids of formula II, well known in the art, wherein $R_2$ is other than hydrogen, e.g., lower alkyl by selectively alkylating the $\Delta^{9(10)}$-compounds of formula XVII-1 with a lower alkyl halide in the presence of a strong base, preferably lithium in liquid ammonia at temperatures in the order of $-40°$ C in an inert solvent such as, for example, diethyl ether by means known in the art.

Moreover, when $R_{15}$ of the β-keto ester or other analogs thereof of the formula IV-a is oxo and not in a protected ketal form, $\Delta^4$, $\Delta^{9(10)}$-steroids of formula III in lieu of the steroids of formula II will be produced in accordance with Reaction Scheme E. Thus, in a specific embodiment exemplified in Reaction Scheme E, steroids encompassed by the genus of the formula III are prepared. The dione ester of the formula V-a-4 is reacted with the methylene ketal of formula IV-a-1 in accordance with Step (a) in the presence of an alkali alkoxide such as 0.1 N sodium methoxide in a methanol solvent using a temperature range of 0° C–20° C to yield the substituted trione of formula XVI-a. The compound of formula XVII-a in accordance with Step (b) of Reaction Scheme E can be hydrolyzed and ring closed using a hydrogen halide acid such as hydrogen bromide in an acetone solvent at a temperature of approximately 20° C to yield the acid compound XVII-a. Decarboxylation of compound XVII-a in refluxing toluene in accordance with Step (c) yields compound XVII-1-a. The diene steroids of the formula III-a can be obtained in accordance with Step (d) of Reaction Scheme E by cyclizing the compound of formula XVII-1-a using an alkali alkoxide preferably potassium t-butoxide in benzene. The 17-hydroxy diene steroids of formula III-b are obtained in accordance with Step (e) of Reaction Scheme E by refluxing in methanol in the presence of acid, preferably hydrogen chloride.

REACTION SCHEME E

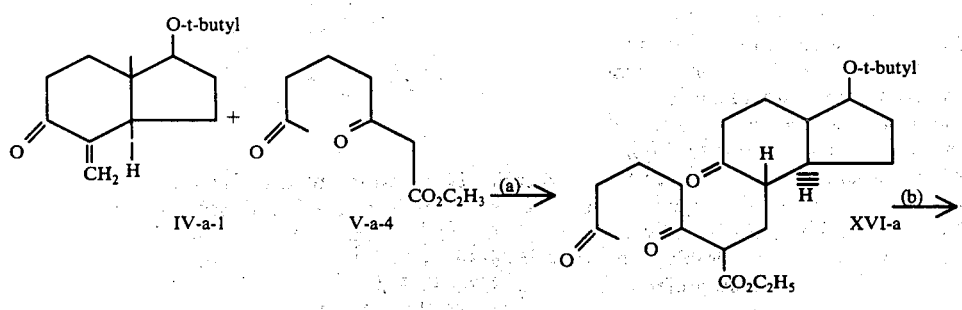

-continued
REACTION SCHEME E

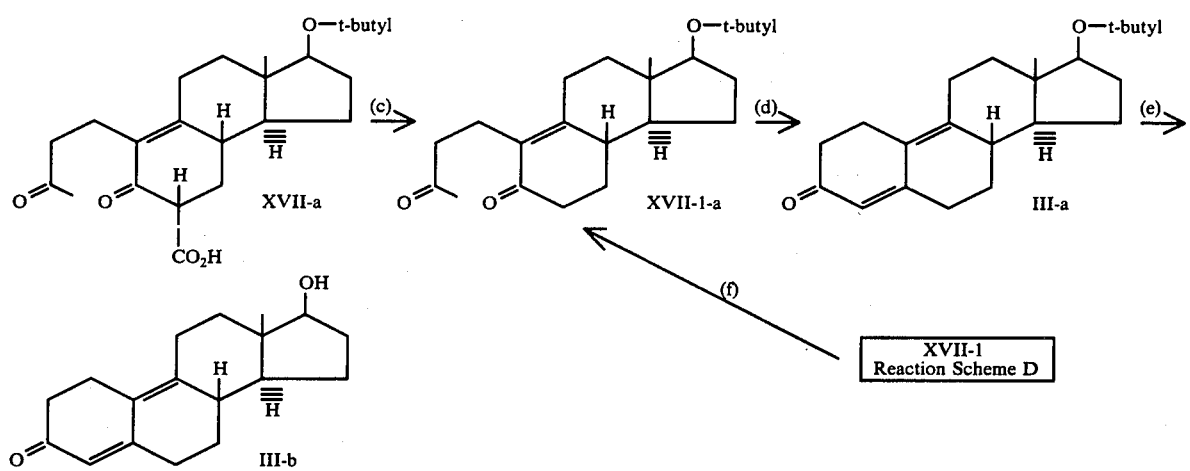

The keto compound XVII-1 of Reaction Scheme D can also be converted to steroids of the formula XVII-1-a via mild hydrolysis of the ketal moiety employing 0.1 N hydrochloric acid in a solvent such as tetrahydrofuran at a temperature of approximately 20° C in accordance with Step (f) of Reaction Scheme E. Steroids of Formula III can be converted to pharmaceutically valuable estrogens by known means (cf. Velluz et al., Angewandte Chemic 72, 725 (1960).

In a further aspect, the present invention relates to the preparation of Δ⁴, Δ⁹⁽¹⁰⁾-steroids of the formula III by reacting a vinylogous beta keto ester or other analogs of the formula

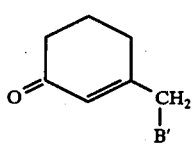

VI wherein B' is defined as aforesaid
with compounds of the formula IV-a and IV-c.

A preferred value of B' is lower alkoxy carbonyl. Especially preferred is methoxy carbonyl and ethoxy carbonyl. Thus, in a specific embodiment exemplified in Reaction Scheme F, diene steroids of the formula III-b are prepared. The vinylogous beta keto ester of formula VI-a is reacted with the methylene ketone of formula IV-a-1 in accordance with Step (a) of Reaction Scheme F in the presence of an alkali lower alkoxide, preferably 0.1 N sodium methoxide in a lower alcohol solvent, preferably, methanol or ethanol, at a temperature range of 0° C to 20° C yielding the dione of formula XXIII. The dione steroid of formula III-b can be conveniently obtained from the compound of formula XXIII by cyclization using refluxing mineral acid, preferably, 1-N-hydrochloric acid in a lower alcohol solvent, preferably methanol.

REACTION SCHEME F

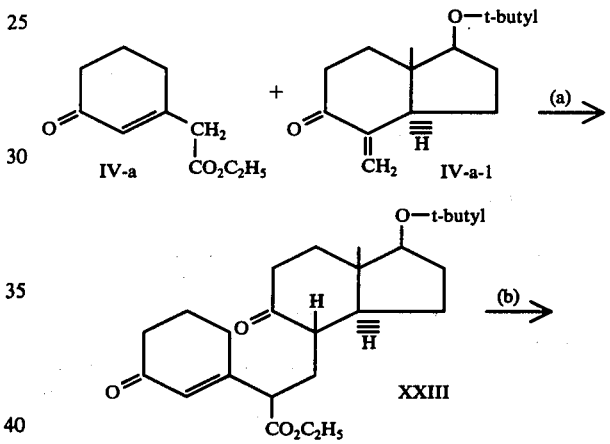

In still another aspect of this invention, compounds of the formula IV-f, in Reaction Scheme A, can be converted to compounds of the of the formula XXIII below, which are subgeneric to the compounds of formula IV

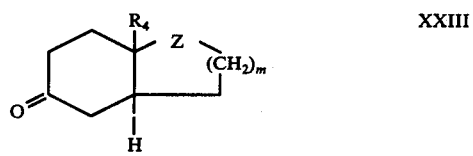

XXIII wherein R₄, Z and m are as defined aforesaid
by decarboxylation in a refluxing solvent such as, for example, tetrahydrofuran or toluene with or without a strong mineral acid, e.g., hydrochloric acid. The novel C/D-trans bicyclic indanone of compounds of formula XXIII are themselves useful intermediates in a total steroidal synthesis by employing, e.g. the methods described by R. E. Ireland and M. Chaykovsky, J. Org. Chem. 28, 748 (1963) the compounds of formula XXIII can be converted to their $\Delta^\alpha$ acid analogs by a bromination-dehydrobromination procedure. The $\Delta^\alpha$-C/D trans indanones can be converted by methods described in the above cited reference to the tricyclic compounds of the formula I which in turn can be converted to pharmaceutically valuable steroids by procedures hereinafter described.

In a further aspect, the synthesis of the present invention relates in accordance with Step (11) of Reaction Scheme B to the preparation of 2,3,3a,4,5,7,8,9,9a,9b-decahydro-3a-alkyl-7-oxo-1H-benz[e]indenes and 4,4a$\beta$,4b$\alpha$,5,6,7,8,8a,9,10-decahydro-8a$\beta$-alkyl-3H-phenanthrene-3-ones which contain in the 3-position and 8-position, respectively, an oxo substituent or a $\beta$-OR$_2$ moiety wherein R$_2$ has the meaning given in the text accompanying formula I. Many members of this class of known compounds which are valuable intermediates in the synthesis of steroids, for example, benz[e]indene derivatives contain asymmetric centers at positions-9a,9b,3a and also at the 3-position if the substituent thereat is other than oxo. Thus, of the 3-oxo compounds, there are eight possible different stereoisomers, whereas of the compounds containing a 3-OR$_2$ substituent, there are possible sixteen stereoisomers.

In a preferred embodiment of this aspect, the synthesis relates to the preparation of the 9a$\beta$, 9b$\alpha$,3a$\beta$-stereoisomers of the benz[e]indene series, its optical antipode and racemate thereof and in the case where the 3-substituent is other than oxo, the 9a$\beta$,9b$\alpha$,3a$\beta$,3$\beta$-stereoisomer, its optical antipode and the racemate thereof. The corresponding phenanthrene-2-ones, i.e., 4a$\beta$,4b$\alpha$,8a$\beta$-stereoisomers may also be prepared. The especially desired end-products of the synthesis of this invention are the (−)-enantiomers of the formula wherein R$_1$, R$_4$, Z and $m$ are as defined aforesaid.

The compounds of formula I can be obtained by commencing the synthesis of this invention with an optically pure starting material of formula IV or by commencing the synthesis of this invention with a racemic (i.e., dl) starting material of the formula IV and effecting resolution at any intermediate stage or after the desired end-product of formula I has been obtained as the racemate.

Referring to Reaction Scheme G, wherein the compounds are assigned Roman numerals for identification schematically, the sequence of reactions involved in the synthesis of a specific embodiment, namely, the benz[e]indenes of formula I-a are illustrated. Thus, ethylpropionylacetate is reacted with a compound of formula IV-c-1 wherein the leaving group "X" exemplified is mesyloxy (compounds of formula IV-a-1 can also suitably be employed) to yield compounds of formula XV in accordance with Step ($a$). Reaction conditions employed for this conversion are identical with that exemplified hereinabove in process step ($a$) of Reaction Scheme E for the preparation of compound XVI. Compound of formula I-a is obtained in accordance with process step ($b$) via cyclization which includes an internal aldol condensation and dehydration using a strong mineral acid, e.g., 2N-hydrochloric acid in a lower alcohol solvent, e.g., methanol, at the reflux temperature of the solvent. The conversion of compounds of the formula XV of Reaction Scheme G to compounds of the formula I-a can also be conducted under reaction conditions employed in Steps ($b$), ($c$) and ($e$) of Reaction Scheme D.

As indicated above, the 2,3,3a,4,5,7,8,9,9a$\beta$,9b$\alpha$-decahydro-3a$\beta$-alkyl-7-oxo-1H-benz[e]indenes and the 4,4a$\beta$,4b$\alpha$,5,6,7,8,8a,9,10-decahydro-8a$\beta$-alkyl-3H-phenanthren-2-ones of formula I obtained by the process of this invention are useful as intermediates in the formation of the tetracyclic steroid nucleus in accordance with Reaction Scheme F. The benz[e]indenes and the phenanthren-2-ones are a known class of compounds. The benz[e]indenes, for example, can be converted into the tetracyclic steriod nucleus by condensing the 7-oxo-benz[e]indene with for example, methyl-vinyl ketone or 1,3-dichloro-2-butene according to methods known per se. The patent literature contains many references which are illustrative of methods to effect conversion of the tricyclics of formula I to known steriods of which U.S. Pat. Nos. 3,115,507; 3,120,544; 3,128,591; 3,150,152 and 3,168,530 are exemplary.

REACTION SCHEME G

Preparation of the tricyclic compounds of Formula I

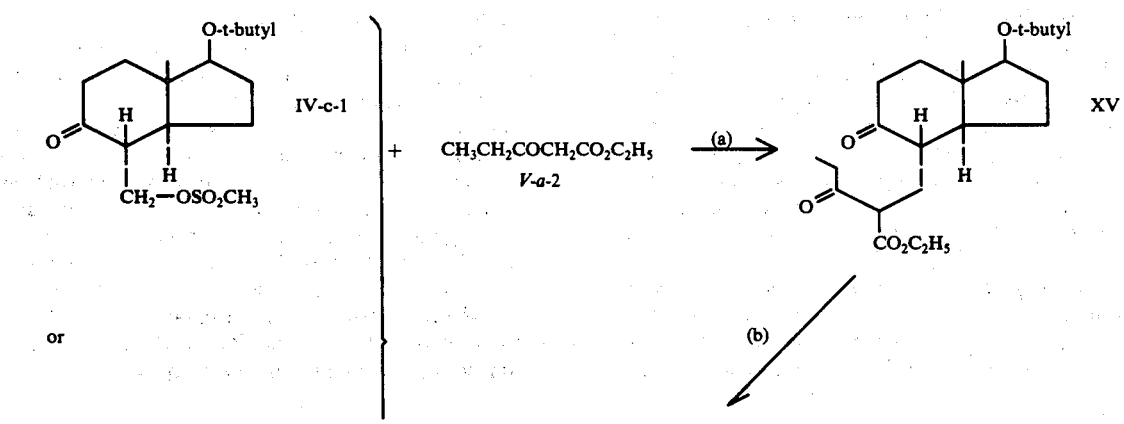

-continued
REACTION SCHEME G

Preparation of the tricyclic compounds of Formula I

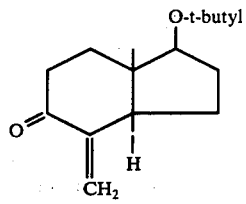   IV-a-1

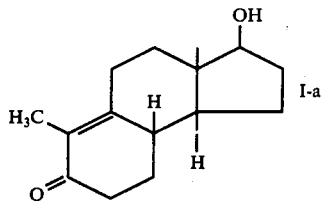   I-a

The ultimate utility of the tricyclic intermediates depends on the nature of $R_1$ and $R_4$. For example, compounds wherein $R_1$ is hydrogen may lead to either 19-nor steroids (Velluz et al., Angewandte Chemie 72, 725, (1960); or alternatively to 10α-19-nor-steroids (French Pat. No. 1,360,55) depending upon the reaction conditions. Further, the tricyclics wherein $R_1$ is hydrogen may be converted into 19-nor-retro(9β,10α)-steroids (Velluz et al., Tetrahedron suppl. 8, Part II, 495 (1966) and estrogens, viz — compounds having an aromatic "A" ring — e.g., estradiol (Velluz et al., Angewandte Chemie 72, 725 (1960). On the other hand, compounds wherein $R_1$ is alkyl may lead to compounds of the 9α,-10α-series (Velluz et al., Angewandte Chemie 77, 185, (1960) or alternatively to compounds of the retrosteroid series viz — those having inverted centers of asymmetry at positions $C_9$ and $C_{10}$, i.e., the 9β,10α-steroids (Belgium Pat. No. 663,193). Compounds wherein $R_1$ is lower alkyl may be obtained wherein $R_6$ of the compounds of formula V-b is lower alkyl (other than methyl).

As illutrated by the following Reaction Scheme II, in the first step of this reaction, the cyclo-olefin I may be hydrogenated to the tricyclic compound XIX. The reaction is preferably effected with a noble metal catalyst, e.g., a palladium-charcoal or a lower-rhodium charcoal catalyst. In formula XIX, $R_1$ represents hydrogen or lower alkyl. Thus, compounds of formula I wherein $R_1$ represents hydrogen or alkyl can be hydrogenated to the compounds of formula XIX. The conversion of compounds of formula I to compounds of formula XIX and of the latter to compounds of formula XXII are described in greater detail in Belgium Pat. No. 663,197.

Tricyclic compounds of formula I for values wherein $R_1$ is hydrogen may be converted by means known in the art to compounds of formula XXI wherein $R_1$ is hydrogen viz — steroids of the 19-nor-10α-series. Further, the tricyclic compounds of formula I wherein $R_1$ is hydrogen may be alternatively converted to compounds of formula II viz — the normal steroids of the 9α,10β-(normal-19-nor series. This is described more fully in Angewandte Chemie 77, 185 (1965), Velluz, Valls and Nominé and Angewandte Chemie 72, 725 (1960), Velluz et al.

A preferred procedure for converting tricyclic compounds of formula I wherein $R_1$ is hydrogen to normal steroids of the 9α-19-nor series of formula II can be effected by reacting the tricyclic compounds with 4-halo-2-alkoxy butane wherein the halogen is preferably selected from the group consisting of chlorine, bromine or iodine. For example, a tricyclic compound of formula I such as 2,3,3a,4,5,7,8,9aβ,9bα-decahydro-3aβ-ethyl-3-oxo-7-oxo-1H-benz[e]indene may be reacted with for example, 4-chloro-2-tertiarybutoxy-butane in a suitable solvent such as, for example, dimethylformamide or dimethylsulfoxide under a nitrogen atmosphere in the presence of a base such as, for example, sodium hydride or potassium tertiarybutoxide at a temperature range of between 15° and 100° to yield the intermediate 10-[3-tertiarybutoxy-butyl]-13-ethyl-19-nor-desA-androst-9-ene-5,17-dione. This latter compound can be converted to norgestrel by procedures described more fully in U.S. Patent application of Gabriel Saucy, Ser. No. 679,989, filed on Nov. 2, 1967.

4-Halo-2-tertiarybutoxy may be prepared from 4-halo-2-butanol by reaction of the latter compound with isobutylene in the presence of a mineral acid such as sulfuric acid or hydrochloric acid at room temperature.

The tricyclic compounds of formula I for values wherein $R_1$ is alkyl may be converted by methods known in the art to compounds of formula XXII viz — steroids of the "retro" series via catalytic hydrogenation compounds of the formula XIX and base catalyzed reaction with for example, methyl vinyl ketone.

REACTION SCHEME H

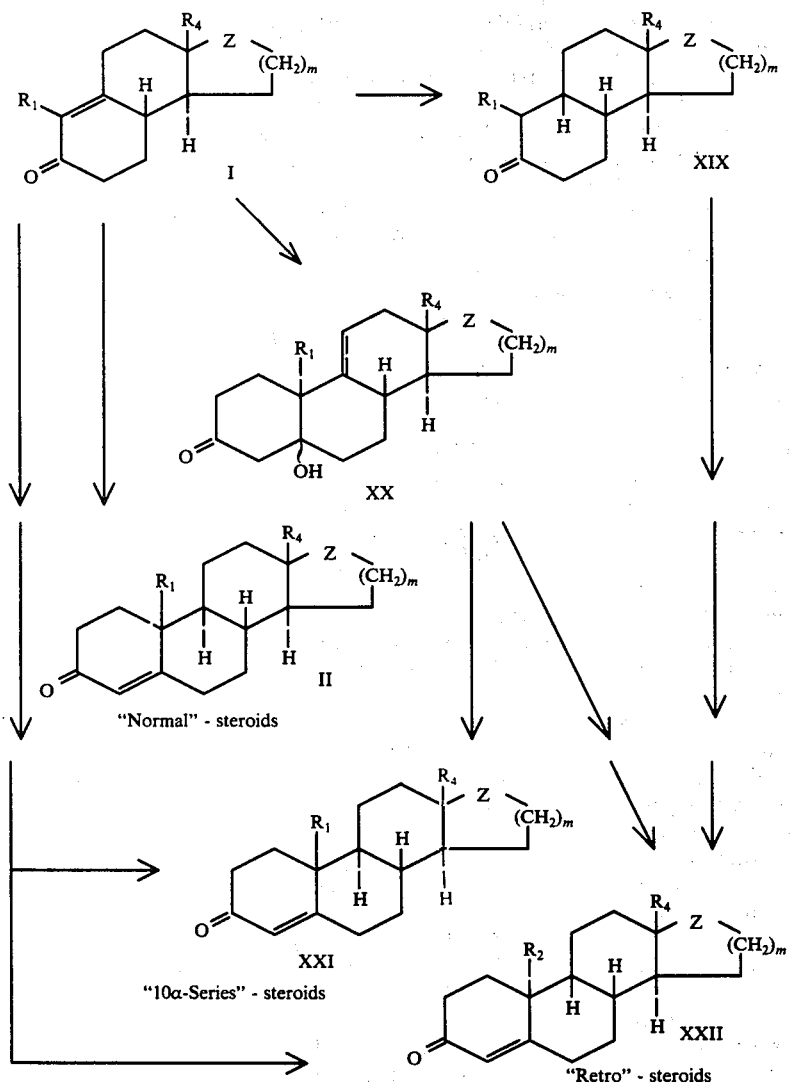

Compounds of formula I can also be directly reacted with for example, methyl vinyl ketone yielding a 5-hydroxy-tetracyclic compound of formula XX. These latter compounds can then be subjected to dehydration followed by hydrogenation or to hydrogenation followed by dehydration to yield a 9β,10α- or 10α-steroids of formulae XXI and XXII. These procedures are described in greater detail in Netherlands Octrooiaanvrage No. 6,412,939. Still other methods of utilizing compounds of formula I are described in the literature or in the patents.

Compounds of formula I when converted into compounds of formula II wherein $R_4$ is ethyl and $R_1$ is hydrogen and Z is carbonyl can be selectively alkynylated by a suitable organic metallic acetylide affording norgestrel (13β-ethyl-17α-ethinyl-17-hydroxy-gon-4-ene-3-one). The latter compound can also be prepared according to Reaction Scheme D (cf. Page 39 herein). Exemplary of the suitable alkynylating agents to effect conversion to norgestrel are the alkali acetylides such as lithium acetylide, potassium acetylide, sodium acetylide, etc. The reaction is carried out in the presence of liquid ammonia in suitable solvent systems such as benzene or toluene. The alkynylation is effected preferably at the reflux temperature of the reaction medium although temperatures from —60° to —30° are suitable. Exemplary of other suitable reagents to effect the acetylenic addition are ethylaminediamine complex in dimethylformamide solvent and Grignard analogs such as mono and bis acetylene-magnesium halides by means known in the art.

Further, the 19-nor-compounds of formula II, wherein $R_4$ is propyl are evulatory inhibitors (of., Tetrahedron Letters 127 (1961), Velluz, Nominé et al.). Additionally, compounds of formula I wherein $R_4$ is methyl and $R_1$ is hydrogen have been converted to the series of formula II, specifically, 19-nortestosterone acetate, J. Org. Chem., 26, 3904 (1961), L. J. Chinn and H. L. Dryden.

Moreover, compounds of formula I wherein $R_4$ is ethyl and $R_1$ is methyl and "$m$" is equal to 2 can be converted to compounds of formula XXII, i.e., 18-homo-retrosteroids, specifically the acetyl derivatives of the pregnane series, which are progestational agents and thus useful in the treatment of fertility disorders. The 18-homo-retroandrostanes of this series have both anti-estrogenic and anti-androgenic activity effecting the secretion of gonadotropic hormones. Hence, these compounds can be used for example, in the treatment of gynecological disorders and as contraceptive agents.

The methods of this invention, as indicated above, result in the preparation either of the desired optical enantiomer illustrated by formulae I and II or the racemate thereof. The optical antipode illustrated by formulae I and II can be obtained either by resolution of the corresponding racemic end product or by resolution of racemic starting material or, if racemic starting material is directly subjected to the methods of this invention, resolution of any intermediate racemate. The present invention provides a facile synthesis for optically active end products as a result of the fact that optical specificity is preserved throughout the synthesis as a result of the stereo selectivity of the individual process conversions exemplified in Reaction Schemes A, B, C, D, E and F. Resolution can be effected by conventional resolution means known per se. For example, compounds in which the moiety represented by the symbol "Z" is hydroxy-methylene, or a group convertible into hydroxymethylene such as carbonyl (convertible by reduction to hydroxy-methylene) or an ether or ester of hydroxy-methylene (convertible by hydrolysis to hydroxy-methylene), can be resolved by reacting the compound containing the hydroxy-methylene moiety with a dibasic acid to form a half-acid ester. If the dibasic acids are, for example, dibasic-lower alkanoic acids such as oxalic acid, malonic acid, succinic acid, glutaric acid, adipic acid or the like, or an aromatic dibasic acid such as phthalic acid, the so-formed half-acid ester is then reacted to form a salt with an optically active base such as brucine, ephedrine or quinine and the resulting diastereoisomeric products are separated. Alternatively, the hydroxy-methylene moiety can be esterified with an optically active acid such as camphorsulfonic acid and the resulting diastereoisomeric esters can be separated. The optical antipodes can be regenerated from the separated diastereoisomeric salts and esters by conventional means.

The following examples are illustrative but not limitative of the invention. All temperatures are stated in degrees Centigrade. Infrared, ultraviolet and nuclear magnetic resonance spectra where taken were consistent with stated structures. IR spectra where indicated were taken in chloroform. UV spectra where indicated were taken in ethyl alcohol.

EXAMPLE 1

A 0.5 weight percent solution of 1$\beta$-tertiarybutoxy-5,6,7,7a-tetrahydro-7a$\beta$-methyl-5-oxo-indane in absolute ethanol was hydrogenated at atmospheric pressure and room temperature using a ten percent palladium/-CaCO$_3$ catalyst. Hydrogenation was stopped after the uptake of 1 mole of hydrogen. The solution was then filtered and evaporated in vacuo to give a crude hydrogenation product. This crude product was then subjected to hydrolysis by stirring and refluxing for six hours with a 1:1 mixture of tetrahydrofuran and 2 N hydrochloric acid under a nitrogen atmosphere. The solution was then cooled by means of an ice bath and neutralized with 5 N sodium hydroxide. The solvent was then evaporated in vacuo and the residue was extracted sequentially with ethyl acetate and then ether. The extract was washed with a saturated sodium chloride solution and then dried over sodium sulfate. Evaporation of the solvent in vacuo afforded a mixture of cis and trans reduction products — 3a$\beta$,4,7,7a-tetrahydro-1$\beta$-hydroxy-7a$\beta$-methyl-5(6H)indanone and 3a$\alpha$,4,7,7a-tetrahydro-1$\beta$-hydroxy-7a$\beta$-methyl-5(6H)indanone which was analyzed by vapor phase chromatography and NMR. The vapor phase chromatography consisting of repeatedly subjecting the crude mixture of 3a$\beta$,4,7,7a-tetrahydro-1$\beta$-hydroxy-7a$\beta$-methyl-5(6H)indanone and 3a$\alpha$,4,7,7a-tetrahydro-1$\beta$-hydroxy-7a$\beta$-methyl-5(6H)indanone to vapor phase chromatography in 40 milligram portions on a Barber-Coleman Model 5072 equipped with flame detection and a split ratio of 5:95. By this technique, 3a$\alpha$,4,7,7a-tetrahydro-1$\beta$-hydroxy-7a$\beta$-methyl-5(6H)indanone was obtained as an oil. $\gamma_{max}$ 3620, 3300–3550 and 1715 cm$^{-1}$ in the infrared spectrum.

EXAMPLE 2

110 Mg. of purified trans alcohol 3a$\alpha$,4,7,7a-tetrahydro-1$\beta$-hydroxy-3a$\beta$-methyl-5(6H)indanone was oxidized by reacting with 0.175 ml. of 8 N chromium trioxide in sulfuric acid in a medium of 5 ml. of acetone under a nitrogen atmosphere at 10° C over approximately a five minute period. The reaction mixture was quenched by the addition of 5.0 ml. of ice water and the organic solvent was removed in vacuo. The aqueous solution was then extracted with a mixture of ethyl acetate and ether. The organic phase was washed with sodium bicarbonate and a saturated sodium chloride solution. The extract was dried over sodium sulfate and evaporated in vacuo to give the crude oxidation product 3a$\alpha$,4,7,7a-tetrahydro-7a$\beta$-methyl-1,5-(6H)indanedione, as an oil. 68 Mg. of the crude oxidation product, 3a$\alpha$,4,7,7a-tetrahydro-7a$\beta$-methyl-1,5-(6H)indanedione was subjected to vapor phase chromatography in 14 mg. aliquots on a Barber-Coleman Model 5072 equipped with flame detection at a split ration of 5:95. Fractionation gave pure 3a$\alpha$,4,7,7a-tetrahydro-7a$\beta$-methyl-1,5-(6H)-indanedione, as an oil; $\gamma_{max}$ 1740 and 1712 cm$^{-1}$ in the infrared spectrum. A sample was crystallized from ether-petroleum ether, m.p. 52°–53° C.

EXAMPLE 3

45 Ml. of dimethylsulfoxide distilled from calcium hydride was added to a 53 percent dispersion of 1.03 g. of sodium hydride.

In mineral oil which had been previously washed with anhydrous ether and dried under a nitrogen atmosphere. The mixture was stirred at 20° C, and a solution of 5.0 grams of 1$\beta$-tertiarybutoxy-5,6,7,7a-tetrahydro-7a$\beta$-methyl-5-oxo-indane in 45 ml. of dimethylsulfoxide was added at once. The reaction mixture was agitated until hydrogen evolution ceased, approximately four hours thereafter. The dimethylsulfoxide was then distilled off under high vacuo utilizing a bath ketp at a temperature of 75° C. The residue (conjugate anion of 1$\beta$-tertiarybutoxy-5,6,7,7a-tetrahydro-7a$\beta$-methyl-5-oxo-indane) was dissolved in 90 ml. of anhydrous ether and added as rapidly as possible (approximately 2 minutes) to a one liter flask containing a thick slurry of anhydrous solid carbon dioxide in 225 ml. of anhydrous ether. The reaction mixture was stirred vigorously. The slurry was formed by cooling 2–3 ml. of anhydrous ether with a dry ice-methanol cooling mixture and then permitting anhydrous solid carbon dioxide from an inverted tank of "bone dry" carbon dioxide to enter. The tank was connected to the flask with rubber pressure tubing. Two outlets were connected to two drying towers filled with anhydrous calcium sulfate. As the slurry formed and thickened, dry ether was added gradually from an addition funnel until a total of 225 ml. had been added. The reaction mixture was stirred for six hours in a dry ice-methanol cooling bath and allowed to stand at 20° C for 16 hours. 200 Ml. of water containing 50 ml. of 0.1 N sodium hydroxide was added to the ether solution and it was agitated under a nitrogen atmosphere for one hour. The ether and water layers were separated and the ether layer was washed twice with water. The combined aqueous fractions were extracted with ether. The combined ether extracts were dried over sodium sulfate and evaporated in vacuo yielding starting material 1β-tertiarybutoxy-5,6,7,7a-tetrahydro-7aβ-methyl-5-oxo-indane. The aqueous solution was filtered and carefully acidified with 2 N hydrochloric acid to a pH of 2.5 at approximately 0° C. The mixture was extracted twice with benzene and then with ether, washed with a saturated sodium chloride solution, dried over sodium sulfate, filtered and evaporated in vacuo to yield a dry solid the β-keto acid, 1β-tertiarybutoxy-5,6,7,7a-tetrahydro-7aβ-methyl-5-oxo-4-indanecarbocyclic acid, m.p. 153°–160° C. Trituration with ether yielded 1β-tertiarybutoxy-5,6,7,7a-tetrahydro-7aβ-methyl-5-oxo-4-indanecarbocyclic acid, m.p. 156° C. An analytically pure sample of 1β-tertiarybutoxy-5,6,7,7a-tetrahydro-7aβ-methyl-5-oxo-4-indanecarbocyclic acid was obtained by recrystallization from acetone, m.p. 159.5° C.

Analysis calculated for $C_{15}H_{22}O_4$: C, 67.64; H, 8.33. Found: C, 67.63; H, 8.62.

EXAMPLE 4

1.84 Grams of unsaturated β-keto-acid 1β-tertiarybutoxy-5,6,7,7a-tetrahydro-7aβ-methyl-5-oxo-4-indane-carbocyclic acid was dissolved in 92 ml. of absolute ethyl alcohol and hydrogenated in the presence of 184 mg. of 10 percent by weight palladium on barium sulfate catalyst at atmospheric temperature and room temperature. The theoretical amount of hydrogen was consummed in 20 minutes. The solution was filtered and evaporated in vacuo, affording 1β-tertiarybutoxy-3aα-4β-5,6,7,7a-hexahydro-7aβ-methyl-5-oxo-4-indane-carboxylic acid, m.p. 107.5°–109° C. An analytically pure sample of 1β-tertiarybutoxy-3aα-4β-5,6,7,7a-hexahydro-7aβ-methyl-5-oxo-4-indane-carbocyclic acid was obtained by recrystallization from ether, m.p. 114°–114.5° C.

Analysis calculated for $C_{15}H_{24}O_4$: C, 67.13; H, 9.02. Found: C, 66.95; H, 9.09.

EXAMPLE 5

30.7 Mg. of the β-keto acid 1β-tertiary-butoxy-3aα-4β-5,6,7,7a-hexahydro-7aβ-methyl-5-oxo-4-indane-carbocyclic acid was dissolved in 2.5 ml. of tetrahydrofuran to which 2.5 ml. of 2 N hydrochloric acid was added. The reaction mixture was refluxed under a nitrogen atmosphere for approximately six hours. It was then neutralized with 2 N sodium hydroxide and evaporated in vacuo. The residue was extracted with ether and the extract was washed with a small amount of saturated sodium chloride solution, dired over sodium sulfate and evaporated in vacuo to give bicyclic keto alcohol 3aα-4,7,7a-tetrahydro-1β-hydroxy-7aβ-methyl-5(6H)indanone as a waxy solid, m.p. 41°–42°. NMR spectra superimposable to that of 3aα-4,7,7a-tetrahydro-1β-hydroxy-7aβ-methyl-5(6H)indanone, as prepared in Example 1.

Analysis calculated for $C_{10}H_{10}O_2$: C, 71.39; H, 9.59. Found: C, 71.11; H, 9.32.

EXAMPLE 5a

246 Mg. of (±)-1β-tertiarybutoxy-3aα,4β,5,6,7,7a-hexahydro-7aβ-methyl-5-oxo-4a-indanecarboxylic acid was suspended in 6 ml. of concentrated hydrochloric acid and stirred under a nitrogen atmosphere for 2.5 hours at room temperature until the compound had thoroughly dissolved. The flask was sealed under a nitrogen atmosphere and permitted to stand for approximately 20 hours. The solution was then evaporated in vacuo at 30° C. to give a mixture that crystallized to yield a tacky crystalline-type solid upon treatment with acetone. The solid was ground up in 1 ml. of ether and the supernatant decanted to give a crude product, melting point 102°–104° C. (dec.). Recrystallization from ether gave pure (±)-3aα,4β,5,6,7,7a-hexahydro-1β-hydroxy-7aβ-methyl-5-oxo-4a-indanecarboxylic acid, melting point 123° C. (dec.).

EXAMPLE 6

2.95 G. of 1β-tertiarybutoxy-3aα,4β,5,6,7,7a-hexahydro-7aβ-methyl-5-oxo-4α-indane-carbocyclic acid was dissolved in a mixture of 22 ml. of dimethylsulfoxide and 12.2 ml. of 36–38 percent aqueous formaldehyde solution. 1.35 G. of piperidine hydrochloride was added and it was stirred under nitrogen for three hours. 9.35 Mg. of sodium bicarbonate in water (100 ml.) was added to the above reaction mixture. It was then extracted three times with benzene. The extract was washed with water and with a saturated sodium chloride solution, dried over magnesium sulfate, filtered and then evaporated in vacuo to give a crude 1β-tertiarybutoxy-3aα-6,7,7a-tetrahydro-7aβ-methyl-4-methylene-indan-5(4H)-one, as an oil. The crude methylene ketone 1β-tertiarybutoxy-3aα-6,7,7a-tetrahydro-7aβ-methyl-4-methylene-indan-5(4H)-one was purified by preparative thin layer chromatography on silica gel with a fluorescent indicator. The sample was applied at the rate of 30 mg. per plate which measured 8 × 8 × 1 mm. thick. The development was carried out with a mixture of 92.5 percent benzene and 7.5 percent ethyl acetate. The area corresponding to the major component was mechanically removed from the plate and the adsorbent was suspended in ethyl acetate. Filtration through Celite was followed by evaporation in vacuo to afford pure 1β-tertiarybutoxy-3aα-6,7,7a-tetrahydro-7aβ-methyl-4-methylene-indan-5(4H)-one, as an oil which crystallized upon standing in a container filled with dry-ice, m.p. 42.5°–44° C.

Analysis calculated for $C_{15}H_{24}O_2$: C, 76.22; H, 10.24 Found: C, 75.32; H, 10.25.

EXAMPLE 7

410 Mg. of freshly distilled ethyl propionyl acetate was added to 115.2 mg. of the crude methylene ketone 1β-tertiarybutoxy-3aα,6,7,7a-tetrahydro-7aβ-methyl-4-methyleneindan-5(4H)-one. The reaction mixture was cooled to 0° C and 0.87 ml. of 0.1 N sodium methoxide in methanol was added while agitating under a nitrogen atmosphere. The reaction mixture was allowed to stand for approximately 18 hours at 0° C and for an additional 4 hours at 20° C. The mixture was cooled by employing an ice bath and neutralizing with 0.87 ml. of 0.1 N hydrochloric acid. The solvent was then removed in vacuo and the residue was extracted with methylene chloride. The extract was sequentially washed with water and with a saturated sodium chloride solution, dried with sodium sulfate, filtered and evaporated in vacuo to yield crude diketoester 2-(1β-tertiarybutoxy-3aα-4β,5,6,7,7a-hexahydro-7aβ-methyl-5-oxo-4-indanylmethyl)-3-oxo valeric acid ethyl ester.

220 Mg. of the β-diketoester 2-(1β-tertiarybutoxy-3aα,4β,5,6,7,7a-hexahydro-7aβ-methyl-5-oxo-4-indanylmethyl)-3-oxo-valeric acid ethyl ester was dissolved in 4 ml. of methanol to which 4 ml. of 2 N hydrochloric acid was added. The reaction mixture was stirred and refluxed under a nitrogen atmosphere for approximately six hours. The reaction mixture was then cooled by use of an ice bath and neutralized sequentially with 0.4 ml. of 19.5 N sodium hydroxide solution and then with 0.4 ml. of 1.0 N sodium hydroxide solution. The solvent was evaporated in vacuo and the residue was extracted two times with ethyl acetate and once with ether. The combined extract was washed once with water and then two times with a saturated sodium chloride solution. The combined extract was then dried over sodium sulfate, filtered and evaporated in vacuo to give crude 2,3,3a,4,5,7,8,9,9aβ,9bα-decahydro-3β-hydroxy-3aβ-6-dimethyl-1H-benz[e]indan-7-one, an oil that could be crystallized by seeding with an authentic sample. 109 Mg. of the crude BCD-tricyclic compound 2,3,3a,4,5,7,8,9,9aβ,9bα-decahydro-3β-hydroxy-3aβ,6-dimethyl-1H-benz[e]indan-7-one was purified by preparative thin layer chromatography on silica gel with fluorescent indicator. Filtration through Celite followed by evaporation in vacuo gave an oil which crystallized upon seeing with an authentic sample; trituration with a 2:1 mixture of ether gave pure 2,3,3a,4,5,7,8,9,9aβ,9bα-decahydro-3β-hydroxy-3aβ,6-dimethyl-1H-benz[e]indan-7-one, m.p. 131°–133° C.

EXAMPLE 8

134 Mg. of the unsaturated β-keto acid, 1β-tertiarybutoxy-5,6,7,7a-tetrahydro-7aβ-methyl-5-oxo-4-indane carboxylic acid was suspended in 5 ml. of ether. The suspension was cooled to 0° C and 7.6 ml. of a solution of diazomethane in ether (0.076 moles /m.) was added dropwise while stirring. After approximately 10 minutes of stirring, the solution was then evaporated in vacuo to yield the methyl ester, 1β-tertiarybutoxy-5,6,7,7a-tetrahydro-7aβ-methyl-5-oxo-4-indane carboxylic acid ethyl ester, m.p. 73°–76° C. Recrystallization from petroleum ether (boiling point 30° C–60° C) gave analytically pure 1β-tertiarybutoxy-5,6,7,7a-tetrahydro-7aβ-methyl-5-oxo-4-indane carboxylic acid ethyl ester, m.p. 76.5° C–77° C.

Analysis calculated for $C_{10}H_{24}O_4$: C, 68.54; H, 8.63. Found C, 68.41; H, 8.92.

EXAMPLE 9

50 Mg. of the acid, 1β-tertiarybutoxy-3aα,4β,5,6,7,7a-hexahydro-7aβ-methyl-5-oxo-4-indane carboxylic acid was dissolved in 1.0 ml. of ether. The solution was cooled to 0° C and 1.05 ml. of a solution of diazomethane in ether (0.19 mmoles ml.) was added dropwise while stirring. After 15 minutes of stirring, the solution was evaporated to dryness to give the β-keto ester 1β-tertiarybutoxy-3aα,4β,5,6,7,7a-hexahydro-7aβ-methyl-5-oxo-4α-indane carboxylic acid methyl ester, m.p. 112.5° C–113.5° C. Recrystallization from petroleum ether (boiling point 30° C.–60° C.) gave analytically pure 1β-tertiarybutoxy-3aα,4β,5,6,7,7a-hexahydro-7aβ-methyl-5-oxo-4α-indane carboxylic acid methyl ester, m.p. 113.0° C.–113.5° C.

Analysis calculated for $C_{10}H_{25}O_4$ C, 68.05; H, 9.28. Found: C, 68.09; H, 9.49.

EXAMPLE 10

54.4 Mg. of the unsaturated β-keto ester, 1βtertiarybutoxy-5,6,7,7a-tetrahydro-7aβ-methyl-5-oxo-4-indane carboxylic acid ethyl ester, was dissolved in 2.7 ml. absolute ethyl alcohol and hydrogenated in the presence of 18.2 mg. of 10 percent palladium on barium sulfate catalyst at atmospheric pressure and room temperatue. Hydrogen uptake ceased after 15 minutes. The solution was filtered and evaporated in vacuo to give crude 1β-tertiarybutoxy-3aα,4β,5,6,7,7a-hexahydro-7aβ-methyl-5-oxo-4α-indane carboxylic acid methyl ester.

EXAMPLE 11

41 Mg. of the β-keto ester, 1β-tertiarybutoxy-3aα,4β,5,6,7,7a-hexahydro-7aβ-methyl-5-oxo-4α-indane carboxylic acid methyl ester was dissolved in a mixture of 1.25 ml. of methanol and 0.55 ml. of trimethyl erthoformate. The solution was cooled with an ice bath at 0° C and 0.26 ml. of 2N methyl sulfuric acid was added while stirring under nitrogen. After five minutes at 0° C, the mixture was allowed to stand at 20° C for 16 hours. It was cooled with an ice bath and neutralized with 1 N sodium methoxide and methanol. The solvent was evaporated in vacuo and the residue was extracted with ether. The extract was washed with aqueous sodium bicarbonate and with a saturated sodium chloride solution, dried over sodium sulfate, filtered and evaporated in vacuo to give 1β-tertiarybutoxy-3aα,4β,5,6,7,7a-hexahydro-5,5-dimethoxy-7aβ-methyl-4α-indancarboxylic methyl ester, an oil; $\gamma_{max}$ $1728^{-1}$ in the infrared spectrum.

EXAMPLE 12

160 Mg. of the ketal ester, 1β-tertiarybutoxy-3aα,4β,5,6,7,7a-hexahydro-5,5-dimethoxy-7aβ-methyl-4α-indancarboxylic methyl ester was dissolved in 3.5 ml. of dry toluene. The solution was cooled to 0° C and 4.5 ml. of a 20 percent solution of diisobutyl aluminum hydride in toluene was added over a 5 minute period while stirring under nitrogen. After an additional 30 minutes at 0° C, the mixture was allowed to stand at 20° C for 16 hours. It was then cooled with an ice bath and 3.0 ml. of methanol was added carefully while stirring. After 10 minutes at 0° C, it was stirred at 20° C for one hour. The crystalline precipitate was filtered through a pad of "Celite" and it was washed and extracted thoroughly with ethyl acetate. The filtrate was washed with a saturated sodium chloride solution, dried over sodium sulfate, filtered and evaporated in vacuo to give 1β-tertiarybutoxy-3aα,4β,5,6,7,7a-hexahydro-5,5-dimethoxy-7aβ-methyl-4α-indanmethanol, an oil; $\gamma_{max}$ 3575 cm$^{-1}$ in the infrared spectrum.

EXAMPLE 13

31.6 Mg. of the ketal alcohol, 1β-tertiarybutoxy-3aα,4β,5,6,7,7a-hexahydro-5,5-dimethoxy-7aβ-methyl-4α-indanmethanol was dissolved in 1.8 ml. of acetone. The solution was cooled to 5° C and 0.2 ml. of distilled water and 0.03 ml. of 2 N hydrochloric acid was added while stirring. After 20 minutes, the reaction mixture was neutralized with 0.65 ml. of a saturated sodium bicarbonate solution. The acetone was evaporated in vacuo and the residue was extracted with ether. The extract was washed with a saturated sodium chloride solution, dried over sodium sulfate, filtered and evaporated in vacuo to give 1β-tertiarybutoxy-3aα,4β,5,6,7,-

7a-hexahydro-7aβ-methyl-5-oxo-4α-indanmethanol, an oil; $\gamma_{max}$ 3580 and 1695 cm$^{-1}$ in the infrared spectrum.

EXAMPLE 14

17.4 Mg. of the β-keto alcohol, 1β-tertiarybutoxy-3aα,4β,5,6,7,7a-hexahydro-7aβ-methyl-5-oxo-4α-indanmethanol was dissolved in 0.25 ml. of dry pyridine and cooled to 0° C. 8.0 Mg. of methane sulfonyl chloride was added while stirring to 0.56 ml. of dry pyridine. The reaction mixture was then allowed to stand at 20° C for 1.5 hours. It was evaporated to dryness in vacuo and the residue was dissolved in chloroform. The solution was then washed with water and a saturated sodium chloride solution, dried over sodium sulfate, filtered and evaporated in vacuo to give 1β-tertiarybutoxy-3aα,4β,5,6,7,7a-hexahydro-7aβ-methyl-5-oxo-4α-indanmethanol methanesulfonate, as an oil; $\gamma_{max}$ 1705, 1353 and 1175 cm$^{-1}$ in the infrared spectrum.

EXAMPLE 15

22.9 Mg. of the β-keto mesylate, 1β-tertiarybutoxy-3aα,4β,5,6,7,7a-hexahydro-7aβ-methyl-5-oxo-4α-indanmethanol methanesulfonate was dissolved in a mixture of 0.3 ml. of methanol and 0.3 ml. of anhydrous benzene. 59.5 Mg. of ethyl propionyl acetate and 0.7 ml. of 1.0 N sodium methoxide was added and the reaction mixture was stirred at 0° C under nitrogen for two hours and at 20° C for 16 hours. The reaction mixture was neutralized with 0.1 N hydrochloric acid and evaporated to dryness in vacuo. The mixture was then treated twice with toluene and taken to dryness under high vacuo to yield the diketo ester, 2-(1β-tertiarybutoxy-3aα,4β,5,6,7,7a-hexahydro-7aβ-methyl-5-oxo-4-indanylmethyl)-3-oxo-valeric acid ethyl ester, as an oil.

EXAMPLE 16

23.8 Mg. of the crude diketo ester, 2-(1β-tertiarybutoxy-3aα,4β,5,6,7,7a-hexahydro-7aβ-methyl-5-oxo-4α-indanylmethyl)-3-oxo-valeric acid ethyl ester was dissolved in 0.5 ml. of tetrahydrofuran, and 0.5 ml. of 0.2 N sodium hydroxide was added while stirring at 20° C. under nitrogen. The reaction mixture was allowed to stand at room temperature for 16 hours. The solvent was then evaporated in vacuo, the residue was dissolved in water and extracted with chloroform to remove neutral material. The water solution was carefully acidified with 2 N hydrochloric acid and extracted with chloroform. The extract was washed with saturated sodium chloride solution, dried over sodium sulfate and evaporated in vacuo to give the crude β-keto acid, 3β-tertiarybutoxy-2,3,3a,4,5,7,8,9,9aβ,9bα-decahydro-3aβ,6-dimethyl-7-oxo-1H-benz[e]inden-8α-carboxylic acid. 3β-tertiarybutoxy-2,3,3a,4,5,7,8,9,-9aβ,9bα-decahydro-3aβ,6-dimethyl-1H-benz[e]inden-7-one was obtained from the above produced product by refluxing in toluene for 1 hour under a nitrogen atmosphere.

EXAMPLE 17

348 Mg. of the lithium salt of the ketal acid, 4-(2-methyl-1,3-dioxolan-2-yl)butanoic acid was dissolved in 5 ml. anhydrous tetrahydrofuran. The solution was cooled to 0° C and 1.25 ml. of a 1.6 molar solution of methyllithium in diethylether was added dropwise over a period of one hour while stirring under a nitrogen atmosphere. The solution was allowed to rise approximately to 20° C and kept at this temperature over a period of two hours. The reaction mixture was added to crushed ice and the organic solvents were removed in vacuo. The residue was extracted with ether, the extract was washed with a saturated sodium chloride solution, dried with magnesium sulfate, filtered and evaporated in vacuo to give crude 5-(2-methyl-1,3-dioxolan-2-yl)-2pentanone.

EXAMPLE 18

378 Ml. of dimethylsulfoxide which was distilled from calcium hydride was added to a 53 percent dispersion of sodium hydride (29.2 g.) in mineral oil which had been washed with anhydrous hexane and dried under nitrogen. The mixture was stirred under nitrogen and heated slowly to 68°-71° C. After 1.5 hours, the evolution of hydrogen ceased and a turbid grey solution of the sodium salt of the metal sulfinyl carbanion had formed. The solution was cooled to 18° C and 60.6 g. of the ketal ester 4-(2-methyl-1,3-dioxolan-2-yl)-butanoic acid ethyl ester was added over a 40 minute period to the stirred solution at a rate such as to maintain the exothermic reaction temperature at 18°-20° C for one hour. The solution was poured on ice, neutralized with cold 1 N hydrochloric acid and extracted with choroform. The extract was washed with a saturated medium chloride solution, dried over magnesium sulfate, filtered and evaporated in vaccuo to give an oil. Volatile impurities were then removed under high vacuo, bath temperature maintained at 80° C to give the β-keto sulfoxide, 1-methyl-sulfinyl-5-(2-methyl-1,3-dioxolan-2-yl)-2-pentanone.

Analysis calculated for $C_{10}H_{10}O_4S$: C, 51.26; H, 7.74; S, 13.68. Found: C, 50.96; H, 7.55; S, 13.81.

EXAMPLE 19

46.2 Grams of aluminum foil was cut into approximately 3 qt. inch square pieces and placed into a 5 lit. three necked flask, fitted with a nitrogen inlet and held on a shaker in a fume hood. The aluminum cuttings were shaken with a solution of 2 lit. of 1 N aqueous sodium hydroxide for 1-2 minutes, and the alkali was siphoned; the metal was washed two times with 2 lit. of water in an analogous manner. The metal was then amalgamated by shaking for 15 seconds with 2 lit. of a two percent mercuric chloride solution in water. The mercuric chloride solution was then siphoned off and the amalgam was washed twice with 1 lit. of ethyl alcohol and once with ether. All operations were conducted under a nitrogen atmosphere. 40.0 G. of the β-keto sulfoxide, 1-methyl-sulfinyl-5-(2-methyl-1,3-dioxolan-2-yl)-2-heptanone was dissolved in a mixture of 2160 ml. of tetrahydrofuran, 240 ml. of water and 4 ml. of 1 N sodium hydroxide. The solution was added at once to the 1 aluminum amalgam and was shaken under a rapid stream of nitrogen for two hours to entrain the methyl mercaptan formed. The reaction mixture was filtered through a pad of Celite on a sintered glass funnel, and the gelatinous precipitate was washed thoroughly with ether. The mixture was concentrated in vacuo to a volume comprising 50 ml. and extracted with ether. The extract was washed with a sodium chloride solution, dried over sodium sulfate, charcoaled with Norit A, filtered and evaporated in vacuo to yield the cetal ketone, 5-(2-methyl-1,3-dioxolan-2-yl)-2-pentanone.

Analysis calculated for $C_9H_{10}O_3$: C, 62.76; H, 9.36. Found: C, 63.09; H, 9.42.

EXAMPLE 20

11.8 Grams (0.1 moles) of diethyl carbonate in 12.5 ml. of anhydrous ether was added to 4.55 g. (0.1 moles) of a 53 percent dispersion of sodium hydride in mineral oil which was washed with anhydrous hexane and dried under nitrogen. This mixture was stirred under nitrogen and 8.6 g. (0.05 mole) of the ketal ketone, 5-(2-methyl-1,3-dioxolan-2-yl)-2-pentanone was added dropwise over a period of two hours. A gentle reflux was maintained throughout the addition and the refluxing was continued for an additional period of approximately 1½ hours. The solution was then cooled with an ice bath, 20 ml. of anhydrous ether and 2 ml. of absolute ethyl alcohol was added and it was stirred for 45 minutes to destroy any unreacted sodium hydride. The suspension was diluted with an equal volume of ether and the ice cold suspension was then added to a rapidly agitated mixture of 6 ml. of glacial acetic acid and 200 ml of ice water. The etheral layer was separated, and the aqueous layer was additionally extracted twice with ether. The extract was washed with saturated sodium bicarbonate and with a saturated sodium chloride, dried with sodium sulfate, filtered and evaporated in vacuo to give the crude β-keto ester, 6-(2-methyl-1,3-dioxolan-2-yl)-3-oxo-hexanoic acid ethyl ester, b.p. 110°-112° C at 0.2 mm.

Analysis calculated for $C_{12}H_{20}O_5$: C, 59.00; H, 8.25. Found: C, 58.92; H, 8.38.

EXAMPLE 21

A mixture of 2.36 g. (0.01 moles) of freshly prepared crude methylene ketone, 1β-tertiarybutoxy-3aβ,6,7,7a-tetrahydro-7aβ-methyl-4-methyleneindan-5(4H):ono and 2.68 g. (0.11 moles) of β-keto ester 6-(2-methyl-1,3-dioxolan-2-yl)-3-oxo-hexanoic acid ethyl ester was cooled in an ice bath. 20 Ml. of an 0.1 normal sodium methoxide solution in methanol was added to the above reaction mixture and the solution was allowed to stand at 0° C for approximately 64 hours and at 20° C for about four hours. The pH of the solution was then adjusted to 7.5 by means of 0.5 N hydrochloric acid and the methanol was evaporated in vacuo. The oily residue was dissolved in 77.5 ml. of tetrahydrofuran to which 77.5 ml. of 0.2 N aqueous sodium hydroxide was added. The reaction mixture was stirred at 20° C under a nitrogen atmosphere for six hours. The tetrahydrofuran was evaporated in vacuo and the basic solution extracted with ether. The ether extract was then washed with water and a saturated sodium chloride solution, dired with sodium sulfate, filtered and evaporated in vacuo to give a neutral impurity. 42.5 Ml. of an aliquot of the aqueous basic solution was carefully acidified at 0° C with 5.1 ml. of 0.5 N hydrochloric acid so as to attain a pH of 3.5. The reaction mixture was then immediately extracted with ethyl acetate and with ether. The combined extract was washed with saturated sodium chloride solution, dried over sodium sulfate, filtered and evaporated in vacuo to give the crude unsaturated β-keto acid, 3β-tertiarybutoxy-2,3,3a,4,5,7,8,9,9aβ,9bβ-decahydro-6-[2-(2-methyl-1,3-dioxolan-2-yl)ethyl]-3aβ-methyl-7-oxo-1H-benz[e]inden-8α-carboxylic acid, an amorphous solid. A few drops of ether were added to the crude solid 3β-tertiarybutoxy-2,3,3a,4,5,7,8,9,-9aαβ,9bα-decahydro-6-[2-(2-methyl-1,3-dioxolan-2-yl)ethyl]-3aβ-methyl-7-oxo-1H-benz[e]-inden-8α-carboxylic acid and it was kept at −10° C for 72 hours. A large crystalline crop was formed, which could be purified by trituration at room temperature with petroleum ether (b.p 30°-60° C). Recrystallization from ether gave analytically pure 3β-tertiary-butoxy-2,3,3a,4,5,7,8,9,-9aβ,9bβ-decahydro-6-[2-(2-methyl-1,3-dioxolan-2-yl)ethyl]-3aβ-methyl-7-oxo-1H-benz[e]inden-8α-carboxylic acid, m.p. 129° C.

Analysis calculated for $C_{25}H_{38}O_6$: C, 69.09, H, 8.81. Found: C, 68.84; H, 8.70.

EXAMPLE 22

Crude unsaturated β-keto acid, 3β-tertiarybutoxy-2,3,3a,4,5,7,8,9,9aβ,9bα-decahydro-6-[2-(2-methyl-1,3-dioxolan-2-yl)ethyl]-3aβ-methyl-7-oxo-1H-benz[e]inden-8α-carboxylic acid was dissolved in 50 ml. of toluene. The solution was stirred and refluxed under nitrogen for 30 minutes. It was then cooled to room temperature and extracted with 0.5 N sodium bicarbonate solution and then with a saturated sodium chloride solution. The toluene solution was then dried over sodium sulfate and evaporated in vacuo to give the unsaturated keto compound 3β-tertiary-butoxy-1,2,3,3a,4,5,8,9,9aβ,9bα-decahydro-6-[2-(2-methyl-1,3-dioxolan-2-yl)ethyl]-3aβ-methyl-7H-benz[e]inden-7-one as an oil. Similar treatment of pure β-keto acid 3β-tertiarybutoxy-2,3,3a4,5,7,8,9,9aβ,9bα-decahydro-6-[2-(2-methyl-1,3-dioxolan-2-yl)ethyl]-3aβ-methyl-7-oxo-1H-benz[e]inden-8α-carboxylic acid gave analytically pure 3β-tertiarybutoxy-1,2,3,3a,4,5,8,9,9aβ,9bα-decahydro-6-[2-(2-methyl-1,3-dioxolan-2-yl)ethyl]-3aβ-methyl-7H-benz[e]-7-one, m.p. 85.5°-86° C. (petroleum ether, b.p. 30°-60° C.);

Analysis calculated for $C_{24}H_{38}O_4$: C, 73.80; H, 9.81. Found: C, 73.77; H, 10.13.

The compound can also exist in a dimorphic modification, m.p. 103.5°-104° C.

EXAMPLE 23

414.7 Mg. of the crude unsaturated keto compound, 3β-tertiarybutoxy-1,2,3,3a,4,5,8,9,9aβ,9bα-decahydro-6-[2-(2-methyl-1,3-dioxolan-2-yl)ethyl]-3aβ-methyl-7H-benz[e]inden-7-one was dissolved in 20.75 ml. of absolute ethyl alcohol containing 0.5 percent by volume of triethylamine. The reaction mixture was hydrogenated in the presence of 145 mg. of a 5 percent palladium on carbon catalyst at 20° C. at atmospheric pressure to give the saturated keto compound, 3β-tertiarybutoxy-1,2,3,3a,4,5,5aα,6,8,9,9aβ,9bα-dodecahydro-6α-[2-(2-methyl-1,3-dioxolan-2-yl)ethyl]-3aβ-methyl-7H-benz-[e]inden-7-one as an oil. Catalytic hydrogenated of a pure crystalline sample of the unsaturated keto compound, 3β-tertiarybutoxy-1,2,3,3a,4,5,8,9,9aβ,9bα-decahydro-6[2-(2-methyl-1,3-dioxolan-2-yl)ethyl]-3aβ-methyl-7H-benz[e]inden-7-one under analogous reaction conditions to that previously described yields analytically pure 3β-tertiarybutoxy-1,2,3,3a,4,5,5aα,6,8,9,-9aβ,9bα-dodecahydro-6α-[2-(2-methyl-1,3-dioxolan-2-yl)ethyl]-3aβ-methyl-7H-benz[e]inden-7-one, m.p. 94.5°-96.0° C (petroleum ether, b.p. 30°-60° C.).

Analysis calculated for $C_{24}H_{40}O_4$: C, 73.43; H, 10.27. Found: C, 73.35; H, 10.52.

EXAMPLE 24

407.2 Mg. of crude 3β-tertiarybutoxy-1,2,3,3a,4,5,-5aα,6,8,9,9aβ,9bα-dodecahydro-6α-[2-(2-methyl-1,3-dioxolan-2-yl)ethyl]-3aβ-methyl-7H-benz[e]inden-7-one was dissolved in 15 ml. of methanol. 15 Ml. of 2 N hydrochloric acid were added to the stirred solution and it was refluxed under nitrogen for four hours. The reaction mixture was neutralized with 3 N sodium hydroxide and evaporated to a small volume in vacuo. The residue was extracted with ethyl acetate. The extract was then washed with saturated sodium chloride solution, dried over sodium sulfate, charcoaled with Norite A, filtered and evaporated in vacuo to give a crude amorphous solid. Trituration with petroleum ether (b.p. 30°-60° C) and finally with 0.3 ml. of ether gave racemic 19-nortestesterone, m.p. 106°-115° C. The noncrystalline material from the mother liquors was purified by preparative thin layer chromatrography on silica gel with a fluorescent indicator. A sample was applied to a single plate measuring 8 inches by 8 inches by 1 mm. thick. The development was carried out with a 50 percent benzene-ethyl acetate mixture and the solvent front was permitted to travel to the top of the plate. The areas corresponding to the product were mechanically removed from the plate and the adsorbent was suspended in ethyl acetate. Filtration through Celite, evaporation in vacuo, purification by trituration with petroleum ether (b.p. 30°-60° C) and ether gave racemic 19-nortestesterone, m.p. 112°-113° C. When using the reverse addition technique (See page 37), racemic 19-nor-testesterone is obtained with m.p. 126°-127° C.

I claim:

1. A process for the preparation of a compound of the formula

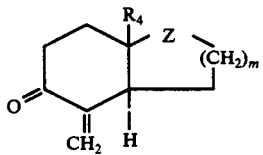

wherein $R_4$ is hydrogen or lower alkyl; Z is carbonyl; m is an integer having the value of 1 or 2, which comprises dissolving a compound of the formula

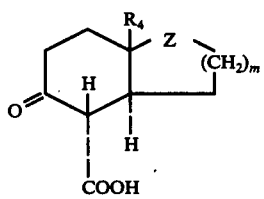

wherein $R_4$, Z and m are as defined above
in dimethylsulfoxide and then adding to the reaction mixture formaldehyde in the presence of a compound selected from the group consisting of methylamine, butylamine, benzylamine and heterocyclic secondary amines and salts thereof derived from strong mineral acids or organic acids at a temperature from about 15° to about 40° C.

* * * * *